US012600805B2

(12) United States Patent
Fujimoto et al.

(10) Patent No.: US 12,600,805 B2
(45) Date of Patent: *Apr. 14, 2026

(54) FLUORINE-CONTAINING ALKYL AMMONIUM BORATE COMPOUND AND METHOD FOR PRODUCING SAME

(71) Applicant: AGC INC., Tokyo (JP)

(72) Inventors: Takuya Fujimoto, Tokyo (JP); Yosuke Ochi, Tokyo (JP)

(73) Assignee: AGC INC., Tokyo (JP)

( * ) Notice: Subject to any disclaimer, the term of this patent is extended or adjusted under 35 U.S.C. 154(b) by 601 days.

This patent is subject to a terminal disclaimer.

(21) Appl. No.: 18/164,149

(22) Filed: Feb. 3, 2023

(65) Prior Publication Data

US 2023/0183393 A1 Jun. 15, 2023

Related U.S. Application Data

(63) Continuation of application No. PCT/JP2021/031108, filed on Aug. 25, 2021.

(30) Foreign Application Priority Data

Aug. 28, 2020 (JP) ................................ 2020-144177
Nov. 27, 2020 (JP) ................................ 2020-196704
Mar. 9, 2021 (JP) ................................ 2021-037078

(51) Int. Cl.

| | |
|---|---|
| ***C08F 4/52*** | (2006.01) |
| ***C07C 211/63*** | (2006.01) |
| ***C07F 5/02*** | (2006.01) |
| ***C08F 4/64*** | (2006.01) |
| ***C08F 4/6592*** | (2006.01) |

(52) U.S. Cl.

CPC .............. *C08F 4/52* (2013.01); *C07C 211/63* (2013.01); *C07F 5/027* (2013.01); *C08F 4/6592* (2013.01)

(58) Field of Classification Search

CPC .................................... C08F 4/52; C08F 4/64
See application file for complete search history.

(56) References Cited

U.S. PATENT DOCUMENTS 5,132,380 A 7/1992 Stevens et al.
6,489,480 B2 * 12/2002 Rodriguez ......... C07D 295/073 548/950
6,822,057 B2 11/2004 Rodriguez
7,799,879 B2 9/2010 Crowther et al.
7,985,816 B2 7/2011 Crowther et al.
8,580,902 B2 11/2013 Crowther et al.
8,835,587 B2 9/2014 Crowthers et al.
2002/0111265 A1 8/2002 Rodriguez
2002/0115806 A1 8/2002 Rodriguez
2007/0197831 A1 8/2007 Lee et al.
2013/0102745 A1 4/2013 Yabukami et al.
2020/0044154 A1 2/2020 Sugioka et al.
2023/0028045 A1 * 1/2023 Ochi .................. C08F 4/65927

FOREIGN PATENT DOCUMENTS

EP 4 119 533 A1 1/2023
JP 2004-500359 A 1/2004
JP 2005-528407 A 9/2005
JP 2007-530673 A 11/2007
JP 2011-246559 A 12/2011
JP 2019-59795 A 4/2019
WO WO 01/42249 A1 6/2001
WO WO 03/089444 A1 10/2003
WO WO 2010/01 4344 A2 2/2010
WO WO-2018070019 A1 * 4/2018 ............. H05B 33/02

OTHER PUBLICATIONS

Chen et al., "Cocatalysts for Metal-Catalyzed Olefin Polymerization: Activators, Activation Processes, and Structure-Activity Relationships", Chemical Reviews, vol. 100, No. 4, 2000, pp. 1391-1434 (total 44 pages).

* cited by examiner

*Primary Examiner* — Rip A Lee
(74) *Attorney, Agent, or Firm* — Oblon, McClelland, Maier & Neustadt, L.L.P.

(57) ABSTRACT

A compound may be useful as a co-catalyst for polymerizing olefin, diene, and acetylene. A fluorine-containing alkylammonium borate compound of formula (1):

(1)

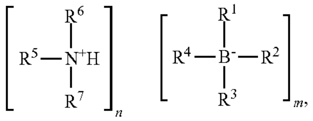

wherein each symbol is as defined in the specification, may be highly active and useful as a co-catalyst used for the polymerization reactions of olefin, diene, and acetylene, compositions containing same. Production methods of such a fluorine-containing alkylammonium borate compound are also provided.

16 Claims, No Drawings

FLUORINE-CONTAINING ALKYL AMMONIUM BORATE COMPOUND AND METHOD FOR PRODUCING SAME

CROSS-REFERENCE TO RELATED APPLICATIONS

The present application is a bypass continuation of international application PCT/JP2021/031108, filed on Aug. 25, 2021, and claims the benefit of the filing date of Japanese Appl. No. 2020-144177, filed on Aug. 28, 2020, Japanese Appl. No. 2020-196704, filed on Nov. 27, 2020, and Japanese Appl. No. 2021-037078, filed on Mar. 9, 2021, the content of each of which is incorporated by reference.

TECHNICAL FIELD

The present invention relates to a fluorine-containing alkylammonium borate compound useful as a co-catalyst for the polymerization of olefin, diene, and acetylene, a composition containing same, and a production method thereof.

BACKGROUND ART

Many reports have been conventionally made on the use of metallocene compound and non-metallocene type metal complex catalysts such as diimine complex, phenoxy complex, and the like as catalysts for the polymerization of olefins, dienes, and acetylenes. As co-catalysts used for stabilizing the cationic active species of these metal complex catalysts, aluminoxanes such as alkylaluminum, methylaluminoxane (MAO) and the like, Broensted acid salts such as ammonium borate and the like, and Lewis acid salts such as triphenylcarbenium borate and the like are used (Non-Patent Document 1).

In the catalyst activation reaction by the aforementioned Broensted acid salt, the leaving group on the metal complex catalyst is protonated and eliminated from the metal complex catalyst to generate a cationic active species of the metal complex catalyst, whereby non-coordinating anions derived from Broensted acid salt stabilize the active species. As the Broensted base constituting the Broensted acid salt, various borate compounds such as tetrakis(pentafluorophenyl)borate, which is a non-coordinating anion, and the like have been reported (Non-Patent Document 1) and, as the Broensted acid, Broensted acids containing nitrogen, phosphorus, oxygen, and/or sulfur are known (Patent Document 1).

As the aforementioned Broensted acid salts, Broensted acid salts (ammonium borates) containing nitrogen such as dimethylanilinium tetrakis(pentafluorophenyl)borate, tri(n-butyl)ammonium tetrakis(pentafluorophenyl)borate, methylpyrrolidinium tetrakis(pentafluorophenyl)borate, and the like are known (Patent Document 2). In the catalyst activation reactions by these ammonium borates, neutral amine compounds are produced due to the loss of proton in the protonation stage. Such neutral amine compound may interact with the cationic active species of the metal complex catalyst, in which case the compound is feared to adversely affect the polymerization reaction.

In order to reduce the basicity of neutral amine compounds generated in the catalyst activation reaction, N-(pentafluorophenyl)pyrrolidinium tetrakis(pentafluorophenyl) borate and the like have been proposed as co-catalysts (Patent Document 3).

DOCUMENT LIST

Non-Patent Document

[Non-Patent Document 1]
Chem. Rev. 2000, 100, 1391-1434

Patent Document

[Patent Document 1]
U.S. Pat. No. 5,132,380
[Patent Document 2]
WO 2010/014344
[Patent Document 3]
WO 2001/042249

SUMMARY OF INVENTION

Problems to be Solved by the Invention

In view of these conventional techniques, the present inventors provide a fluorine-containing alkylammonium borate compound showing, as compared with the prior art, high polymerization activity as a co-catalyst used for the polymerization reactions of olefin, diene, and acetylene by a metal complex catalyst, a composition containing the compound, and an industrial production method thereof.

Means of Solving the Problems

The present inventors conducted intensive studies and found for the first time that a compound represented by the following formula (1):

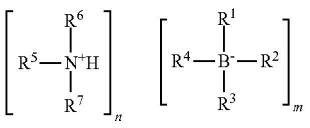

(1)

wherein $R^1$, $R^2$, $R^3$, and $R^4$ are each independently a $C_{6-14}$ aryl group substituted by one or more fluorine atoms or one or more fluoro $C_{1-4}$ alkyl groups, $R^5$ is a $C_{1-30}$ alkyl group substituted by one or more substituents selected from the group consisting of a $C_{6-14}$ aryl group substituted by one or more fluorine atoms, and a fluorine atom, $R^6$ and $R^7$ are each independently an optionally substituted $C_{1-30}$ alkyl group, an optionally substituted $C_{3-15}$ cycloalkyl group, or an optionally substituted $C_{6-14}$ aryl group, or $R^6$ and $R^7$ are bonded to each other to form, together with the nitrogen atom bonded thereto, an optionally substituted cyclic group, n is 1, and m is 1 or 2

(hereinafter to be also referred to as "the compound of the present invention") shows a high metal complex catalyst activation ability and is useful as a co-catalyst in polymerization reactions of olefin, diene, and acetylene, which resulted in the completion of the present invention.

Accordingly, the present invention provides the following.

[1] A compound represented by the following formula (1):

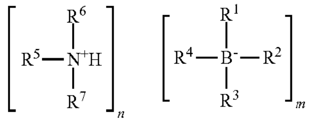

(1)

wherein $R^1$, $R^2$, $R^3$, and $R^4$ are each independently a $C_{6-14}$ aryl group substituted by one or more fluorine atoms or one or more fluoro $C_{1-4}$ alkyl groups, $R^5$ is a $C_{1-30}$ alkyl group substituted by one or more substituents selected from the group consisting of a $C_{6-14}$ aryl group substituted by one or more fluorine atoms, and a fluorine atom, $R^6$ and $R^7$ are each independently an optionally substituted $C_{1-30}$ alkyl group, an optionally substituted $C_{3-15}$ cycloalkyl group, or an optionally substituted $C_{6-14}$ aryl group, or $R^6$ and $R^7$ are bonded to each other to form, together with the nitrogen atom bonded thereto, an optionally substituted cyclic group, n is 1, and m is 1 or 2.

[2] The compound of the aforementioned [1], wherein $R^1$, $R^2$, $R^3$, and $R^4$ are each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 9-phenanthryl group, or a 3-phenanthryl group, each of which is substituted by one or more fluorine atoms or one or more fluoro $C_{1-4}$ alkyl groups.

[3] The compound of the aforementioned [1], wherein all of $R^1$, $R^2$, $R^3$, and $R^4$ are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups.

[4] The compound of any of the aforementioned [1] to [3], wherein $R^5$ is a $C_{1-6}$ alkyl group substituted by a phenyl group or a naphthyl group, each of which is substituted by one or more fluorine atoms, or a fluoro $C_{1-6}$ alkyl group.

[5] The compound of any of the aforementioned [1] to [4], wherein $R^6$ and $R^7$ are each independently a $C_{1-30}$ alkyl group optionally substituted by substituent(s) selected from the group consisting of (1) a $C_{6-14}$ aryl group optionally substituted by halogen atom(s), (2) a halogen atom, and (3) a $C_{1-30}$ alkoxy group; or a $C_{3-8}$ cycloalkyl group optionally substituted by substituent(s) selected from the group consisting of (1) a halogen atom, (2) a $C_{1-30}$ alkyl group, (3) a $C_{1-30}$ alkoxy group, (4) a halo $C_{1-30}$ alkyl group, and (5) a halo $C_{1-30}$ alkoxy group.

[6] The compound of any of the aforementioned [1] to [4], wherein $R^6$ and $R^7$ are bonded to each other to form, together with the nitrogen atom bonded thereto, an optionally substituted cyclic group derived from a 3- to 8-membered monocyclic nitrogen-containing non-aromatic heterocyclic group.

[7] The compound of any of the aforementioned [1] to [4], wherein $R^5$ is a fluoro $C_{1-6}$ alkyl group, $R^6$ and $R^7$ are each independently a $C_{1-30}$ alkyl group optionally substituted by substituent(s) selected from the group consisting of (1) a $C_{6-14}$ aryl group optionally substituted by halogen atom(s), (2) a halogen atom, and (3) a $C_{1-30}$ alkoxy group.

[8] The compound of any of the aforementioned [1] to [7], wherein n and m are each 1.

[9] The compound of any of the aforementioned [1] to [8], wherein a total carbon number of $R^5$, $R^6$, and $R^7$ is not less than 25.

[10] A composition comprising the compound of any of the aforementioned [1] to [9], and a compound of the following formula (2):

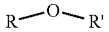

(2)

wherein

R and R' are each independently an optionally substituted $C_{1-30}$ alkyl group, an optionally substituted $C_{3-15}$ cycloalkyl group, or an optionally substituted $C_{6-14}$ aryl group (hereinafter to be also referred to as "the composition of the present invention".

[11] The composition of the aforementioned [10], wherein R and R' are each independently an optionally substituted $C_{1-30}$ alkyl group.

[12] The composition of the aforementioned [10] or [11], wherein a content of the compound represented by the aforementioned formula (2) with respect to 1 mol of the compound represented by the aforementioned formula (1) is 0.01 to 10 mol.

[13] The composition of the aforementioned [10] or [11], wherein a content of the compound represented by the aforementioned formula (2) with respect to 1 mol of the compound represented by the aforementioned formula (1) is 0.1 to 3 mol.

[14] A composition comprising the compound of any of the aforementioned [1] to [9], and a compound of the following formula (3):

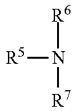

(3)

wherein $R^5$, $R^6$, and $R^7$ are as defined above (in the composition, the compound represented by formula (3) is an amine compound deprotonated from the cation constituting the formula (1) described in the aforementioned [1]).

[15] The composition of the aforementioned [14], wherein a content of the compound represented by the aforementioned formula (3) with respect to 1 mol of the compound represented by the aforementioned formula (1) is 0.01 to 10 mol.

[16] The composition of the aforementioned [14], wherein a content of the compound represented by the aforementioned formula (3) with respect to 1 mol of the compound represented by the aforementioned formula (1) is 0.5 to 3 mol.

[17] The composition of any of the aforementioned [14] to [16], further comprising a compound represented by the following formula (2):

(2)

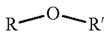

wherein

R and R' are each independently an optionally substituted $C_{1-30}$ alkyl group, an optionally substituted $C_{3-15}$ cycloalkyl group, or an optionally substituted $C_{6-14}$ aryl group.

[18] A co-catalyst for polymerizing at least one monomer selected from the group consisting of olefin, diene, and acetylene, comprising the compound of any of the aforementioned [1] to [9], or the composition of any of the aforementioned [10] to [17].

[19] A method for producing a polymer, comprising polymerizing at least one kind of monomer selected from the group consisting of olefin, diene and acetylene by using the compound of any of the aforementioned [1] to [9] or the composition of any of the aforementioned [10] to [17] as a co-catalyst.

[20] A method for producing a compound represented by the following formula (1):

(1)

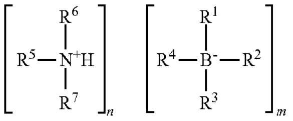

wherein $R^1$, $R^2$, $R^3$, and $R^4$ are each independently a $C_{6-14}$ aryl group substituted by one or more fluorine atoms or one or more fluoro $C_{1-4}$ alkyl groups, $R^5$ is a $C_{1-30}$ alkyl group substituted by one or more substituents selected from the group consisting of (1) a $C_{6-14}$ aryl group substituted by one or more fluorine atoms and (2) a fluorine atom, $R^6$ and $R^7$ are each independently an optionally substituted $C_{1-30}$ alkyl group, an optionally substituted $C_{3-15}$ cycloalkyl group, or an optionally substituted $C_{6-14}$ aryl group, or $R^6$ and $R^7$ are bonded to each other to form, together with the nitrogen atom bonded thereto, an optionally substituted cyclic group, n is 1, and m is 1 or 2, the method comprising a step of reacting, in the presence of a protic acid, a compound represented by the following formula (4):

(4)

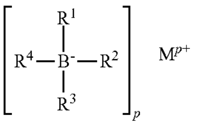

wherein $R^1$, $R^2$, $R^3$, and $R^4$ are as defined above, $M^{p+}$ is an alkali metal ion or an alkaline earth metal ion, and p is 1 or 2, with a compound represented by the following formula (3):

(3)

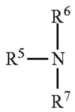

wherein $R^5$, $R^6$ and $R^7$ are as defined above.

Effect of the Invention

According to the present invention, a fluorine-containing alkylammonium borate compound showing a high metal complex catalyst activation ability and useful as a co-catalyst in the polymerization reactions of olefin, diene, and acetylene, a composition containing same, and an industrial production method thereof can be provided.

DESCRIPTION OF EMBODIMENTS

The definitions of the terms and respective symbols used in the present specification are explained below.

In the present specification, the "halogen atom" means a fluorine atom, a chlorine atom, a bromine atom, or an iodine atom.

In the present specification, the "alkyl (group)" means a linear or branched chain alkyl group having a carbon number of not less than 1.

In the present specification, the "$C_{1-30}$ alkyl (group)" means a linear or branched chain alkyl group having a carbon number of 1 to 30. Examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, tetradecyl, hexadecyl, octadecyl, nonadecyl, eicosyl, docosyl, tricosyl, tetracosyl, pentacosyl, hexacosyl, heptacosyl, octacosyl, nonacosyl, triacontyl, and the like.

In the present specification, the "$C_{1-18}$ alkyl (group)" means a linear or branched chain alkyl group having a carbon number of 1 to 18. Examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, tetradecyl, hexadecyl, octadecyl, and the like.

In the present specification, the "$C_{1-6}$ alkyl (group)" means a linear or branched chain alkyl group having a carbon number of 1 to 6. Examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, and the like. Among them, $C_{1-4}$ alkyl group is preferred.

In the present specification, the "halo $C_{1-30}$ alkyl (group)" means the aforementioned "$C_{1-30}$ alkyl" group in which one or more hydrogen atoms are substituted by halogen atom(s). Specific examples thereof include fluoromethyl, difluoromethyl, trifluoromethyl, 2-chloroethyl, 2-bromoethyl, 2-iodoethyl, 2-fluoroethyl, 2,2-difluoroethyl, 2,2,2-trifluoroethyl, pentafluoroethyl, heptafluoropropyl, 2,2-difluoropropyl, 1,1,2,2-tetrafluoropropyl, 2,2,3,3-tetrafluoropropyl, 3,3,3-trifluoropropyl, 2,2,3,3,3-pentafluoropropyl, 2,2-difluorobutyl, 4,4,4-trifluorobutyl, 2,2-difluoropentyl, 5,5,5-trifluoropentyl, 2,2-difluorohexyl, 6,6,6-trifluorohexyl, and the like. Among them, a "fluoro $C_{1-30}$ alkyl (group)" which is a $C_{1-30}$ alkyl group in which the halogen atom in the aforementioned "halo $C_{1-30}$ alkyl (group)" is a fluorine atom, and substituted by one or more fluorine atoms is preferred.

In the present specification, the "halo $C_{1-6}$ alkyl (group)" means the aforementioned "$C_{1-6}$ alkyl" group in which one or more hydrogen atoms are substituted by halogen atom(s). Specific examples thereof include fluoromethyl, difluoromethyl, trifluoromethyl, 2-chloroethyl, 2-bromoethyl, 2-iodoethyl, 2-fluoroethyl, 2,2-difluoroethyl, 2,2,2-trifluoroethyl, pentafluoroethyl, heptafluoropropyl, 2,2-difluoropropyl, 1,1,2,2-tetrafluoropropyl, 2,2,3,3-tetrafluoropropyl, 3,3,3-trifluoropropyl, 2,2,3,3,3-pentafluoropropyl, 2,2-difluorobutyl, 4,4,4-trifluorobutyl, 2,2-difluoropentyl, 5,5,5-trifluoropentyl, 2,2-difluorohexyl, 6,6,6-trifluorohexyl and the like. Among them, a "fluoro $C_{1-6}$ alkyl (group)" which is the aforementioned "halo $C_{1-6}$ alkyl" group in which the halogen atom is a fluorine atom is preferred.

Specific examples of the "fluoro $C_{1-6}$ alkyl (group)" include fluoromethyl, difluoromethyl, trifluoromethyl, 2-fluoroethyl, 2,2-difluoroethyl, 2,2,2-trifluoroethyl, pentafluoroethyl, heptafluoropropyl, 2,2-difluoropropyl, 1,1,2,2-tetrafluoropropyl, 2,2,3,3-tetrafluoropropyl, 3,3,3-trifluoropropyl, 2,2,3,3,3-pentafluoropropyl, 2,2-difluorobutyl, 4,4,4-trifluorobutyl, 2,2-difluoropentyl, 5,5,5-trifluoropentyl, 2,2-difluorohexyl, 6,6,6-trifluorohexyl, and the like. As specific examples of the fluoro $C_{1-6}$ alkyl (group) in the definition of $R^5$, fluoro $C_{1-6}$ alkyl (groups) having fluorine atom(s) at the β-position and/or γ-position such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl and the like are preferred, fluoro $C_{1-4}$ alkyl (groups) having fluorine atom(s) at the β-position such as 2-fluoroethyl, 2,2-difluoroethyl, 2,2,2-trifluoroethyl, pentafluoroethyl, 2,2-difluoropropyl, 2,2,3,3-tetrafluoropropyl, 2,2,3,3,3-pentafluoropropyl, 2,2-difluorobutyl, and the like are more preferred, and fluoro $C_{2-4}$ alkyl (groups) having fluorine atom(s) at the β-position and having 3 or more fluorine atoms such as 2,2,2-trifluoroethyl, 2,2,3,3,3-pentafluoropropyl, and the like are further preferred.

Specific examples of the "fluoro $C_{1-4}$ alkyl (group)" as the substituent of the $C_{6-14}$ aryl group for $R^1$, $R^2$, $R^3$, or $R^4$, or the substituent of the cyclic group formed by $R^6$ and $R^7$ bonded to each other together with the nitrogen atom bonded thereto include fluoromethyl, difluoromethyl, trifluoromethyl, 1,1-difluoroethyl, 2,2,2-trifluoroethyl, pentafluoroethyl, heptafluoropropyl, 1,1,2,2-tetrafluoropropyl, 2,2,3,3-tetrafluoropropyl, 3,3,3-trifluoropropyl, 2,2,3,3,3-pentafluoropropyl, 1,1-difluoropropyl, 2,2-difluoropropyl, nonafluorobutyl, 1,1,2,2-tetrafluorobutyl, 2,2-difluorobutyl, 1,1-difluorobutyl, 4,4,4-trifluorobutyl, and the like. Among them, trifluoromethyl, 1,1-difluoroethyl, pentafluoroethyl, 1,1-difluoropropyl, heptafluoropropyl, 1,1-difluorobutyl, and nonafluorobutyl are preferred, trifluoromethyl, 1,1-difluoroethyl, and pentafluoroethyl are more preferred.

In the present specification, the "cycloalkyl (group)" means a cyclic alkyl group. Unless the carbon number range is particularly limited, it is preferably a $C_{3-15}$ cycloalkyl group, more preferably a $C_{3-8}$ cycloalkyl group.

In the present specification, the "$C_{3-15}$ cycloalkyl (group)" means a cyclic alkyl group having a carbon number of 3 to 15. Examples thereof include cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, and the like. The "$C_{3-8}$ cycloalkyl (group)" means a cyclic alkyl group having a carbon number of 3 to 8. Examples thereof include cyclopropyl, cyclobutyl, cyclopentyl, cyclohexyl, cycloheptyl, cyclooctyl, and the like. Among them, a $C_{3-6}$ cycloalkyl group is preferred.

In the present specification, the "alkoxy (group)" means a group in which a linear or branched chain alkyl group is bonded to an oxygen atom.

In the present specification, the "$C_{1-30}$ alkoxy (group)" means a linear or branched chain alkoxy group having a carbon number of 1 to 30. Examples thereof include methoxy, ethoxy, propoxy, isopropoxy, butoxy, isobutoxy, sec-butoxy, tert-butoxy, pentyloxy, isopentyloxy, neopentyloxy, hexyloxy, isohexyloxy, 1,1-dimethylbutoxy, 2,2-dimethylbutoxy, 3,3-dimethylbutoxy, 2-ethylbutoxy, heptyloxy, octyloxy, nonyloxy, decyloxy, undecyloxy, dodecyloxy, tridecyloxy, tetradecyloxy, hexadecyloxy, octadecyloxy, eicosyloxy, docosyloxy, tricosyloxy, tetracosyloxy, pentacosyloxy, hexacosyloxy, heptacosyloxy, octacosyloxy, nonacosyloxy, triacontyloxy, and the like.

In the present specification, the "$C_{1-6}$ alkoxy (group)" means a linear or branched chain alkoxy group having a carbon number of 1 to 6. Examples thereof include methoxy, ethoxy, propoxy, isopropoxy, butoxy, isobutoxy, sec-butoxy, tert-butoxy, pentyloxy, isopentyloxy, neopentyloxy, hexyloxy, and the like. Among them, a $C_{1-4}$ alkoxy group is preferred.

In the present specification, the "halo $C_{1-30}$ alkoxy (group)" means the aforementioned "$C_{1-30}$ alkoxy" group in which one or more hydrogen atoms are substituted by halogen atom(s). Specific examples thereof include difluoromethoxy, trifluoromethoxy, 2-chloroethoxy, 2-bromoethoxy, 2-iodoethoxy, 2-fluoroethoxy, 2,2-difluoroethoxy, 2,2,2-trifluoroethoxy, pentafluoroethoxy, heptafluoropropoxy, 2,2-difluoropropoxy, 1,1,2,2-tetrafluoropropoxy, 2,2,3,3-tetrafluoropropoxy, 3,3,3-trifluoropropoxy, 2,2,3,3,3-pentafluoropropoxy, 2,2-difluorobutoxy, 2,2,3,3,3-pentafluoropropoxy, 4,4,4-trifluorobutoxy, 2,2-difluoropentyloxy, 5,5,5-trifluoropentyloxy, 2,2-difluorohexyloxy, 6,6,6-trifluorohexyloxy, and the like. Among them, "halo $C_{1-6}$ alkoxy" in which one or more hydrogen atoms in the aforementioned "$C_{1-6}$ alkoxy" group are substituted by halogen atom(s) is preferred.

In the present specification, the "fluoro $C_{1-6}$ alkoxy (group)" means the aforementioned "halo $C_{1-6}$ alkoxy" group in which the halogen atom is a fluorine atom. Specific examples thereof include difluoromethoxy, trifluoromethoxy, 2-fluoroethoxy, 2,2-difluoroethoxy, 2,2,2-trifluoroethoxy, pentafluoroethoxy, heptafluoropropoxy, 2,2-difluoropropoxy, 1,1,2,2-tetrafluoropropoxy, 2,2,3,3-tetrafluoropropoxy, 3,3,3-trifluoropropoxy, 2,2,3,3,3-pentafluoropropoxy, 2,2-difluorobutoxy, 2,2,3,3,3-pentafluoropropoxy, 4,4,4-trifluorobutoxy, 2,2-difluoropentyloxy, 5,5,5-trifluoropentyloxy, 2,2-difluorohexyloxy, 6,6,6-trifluorohexyloxy, and the like. Among them, "fluoro $C_{1-4}$ alkoxy (groups)" such as difluoromethoxy, trifluoromethoxy, 2,2,2-trifluoroethoxy, pentafluoroethoxy, pentafluoroethoxy, 2,2,3,3-tetrafluoropropoxy, 3,3,3-trifluoropropoxy, 4,4,4-trifluorobutoxy, and the like are preferred, difluoromethoxy, trifluoromethoxy, 2,2,2-trifluoroethoxy, pentafluoroethoxy, and pentafluoroethoxy are more preferred, and trifluoromethoxy is particularly preferred.

In the present specification, the "aryl (group)" means a monocyclic or polycyclic (fused) hydrocarbon group showing aromaticity. Specific examples thereof include $C_{6-14}$ aryl groups such as phenyl, 1-naphthyl, 2-naphthyl, 2-biphenylyl, 3-biphenylyl, 4-biphenylyl, 1-anthryl, 2-anthryl, 9-anthryl, 3-phenanthryl, 9-phenanthryl, and the like. Among them, phenyl, 4-biphenylyl, 1-naphthyl, and 2-naphthyl are preferred.

In the present specification, the "$C_{6-14}$ aryl (group) substituted by one or more fluorine atoms or one or more fluoro $C_{1-4}$ alkyl groups" means the aforementioned $C_{6-14}$ aryl group in which one or more hydrogen atoms are substituted by a fluorine atom or a fluoro $C_{1-4}$ alkyl group, Specifically, for example, pentafluorophenyl group, 2,2',3,3',4',5,5',6,6'-nonafluoro-4-(1,1'-biphenylyl) group, 2,3,4,5,6,7,8-heptafluoro-1-naphthyl group, 1,3,4,5,6,7,8-heptafluoro-2-naphthyl group, 4-trifluoromethylphenyl group, 3,4-bis(trifluoromethyl)phenyl group, and the like can be mentioned. Among them, pentafluorophenyl group, 2,2',3,3',4',5,5',6,6'-nonafluoro-4-(1,1'-biphenylyl) group, 2,3,4,5,6,7,8-heptafluoro-1-naphthyl group, and 1,3,4,5,6,7,8-heptafluoro-2-naphthyl group are preferred.

In the present specification, the "$C_{1-30}$ alkyl (group) substituted by a $C_{6-14}$ aryl group substituted by one or more fluorine atoms" means a $C_{1-30}$ alkyl (group) substituted by the aforementioned $C_{6-14}$ aryl group in which one or more hydrogen atoms are substituted by a fluorine atom, and a $C_{1-6}$ alkyl group substituted by a phenyl group or a naphthyl group, each substituted by one or more fluorine atoms, is preferred. Specifically, for example, pentafluorophenylmethyl group, 2,2',3,3',4',5,5',6,6'-nonafluoro-4-(1,1'-biphenylyl)methyl group, 2,3,4,5,6,7,8-heptafluoro-1-naphthylmethyl group, 1,3,4,5,6,7,8-heptafluoro-2-naphthylmethyl group and the like can be mentioned. Among them, pentafluorophenylmethyl group, 2,3,4,5,6,7,8-heptafluoro-1-naphthylmethyl group, or 1,3,4,5,6,7,8-heptafluoro-2-naphthylmethyl group is preferred, and pentafluorophenylmethyl group is more preferred.

In the present specification, the "cyclic group formed by $R^6$ and $R^7$ bonded to each other together with the nitrogen atom bonded thereto" means a cyclic ammonio group derived from a saturated nitrogen-containing non-aromatic heterocyclic group (in the case of the compound of the present invention (compound (1)) or a saturated nitrogen-containing non-aromatic heterocycle (in the case of below-mentioned compound (3)). As used herein, the "cyclic ammonio group derived from a saturated nitrogen-containing non-aromatic heterocyclic group" means a cyclic ammonio group formed by the binding of $R^6$ and $R^7$ to each other and the binding of a hydrogen atom to the nitrogen atom to which $R^6$ and $R^7$ are bonded. Such "cyclic group" may have, besides carbon atom, a hetero atom selected from an oxygen atom, a sulfur atom, and a nitrogen atom as other ring-constituting atom of the nitrogen atom of the amino group, and a cyclic ammonio group derived from a 3- to 8-membered (preferably 4- to 6-membered) monocyclic nitrogen-containing non-aromatic heterocyclic group can be mentioned. Specific examples of the "cyclic group" include cyclic ammonio groups derived from 3- to 8-membered monocyclic nitrogen-containing non-aromatic heterocyclic groups, such as azetidinyl group, azetidinyl group, pyrrolidinyl group, pyrrolinyl group, piperidyl group, azepanyl group, morpholinyl group, thiomorpholinyl group, piperazinyl group, oxazolidinyl group, thiazolidinyl group, imidazolidinyl group, oxazolinyl group, thiazolinyl group, imidazolinyl group, pyrazolidinyl group, pyrazolinyl group, tetrahydropyridyl group, tetrahydropyrimidinyl group, tetrahydrotriazolyl group, and the like. Among them, a cyclic ammonio group derived from azetidinyl group, pyrrolidinyl group, piperidyl group, piperazinyl group, or morpholinyl group is preferred, and a cyclic ammonio group derived from piperidyl group or piperazinyl group is more preferred. As the "saturated nitrogen-containing non-aromatic heterocycle", a 3- to 8-membered (preferably 4- to 6-membered) monocyclic nitrogen-containing non-aromatic heterocycle that may have, besides carbon atom, a hetero atom selected from an oxygen atom, a sulfur atom, and a nitrogen atom as other ring-constituting atom of the nitrogen atom of the amino group can be mentioned. Specific examples of the "saturated nitrogen-containing non-aromatic heterocycle" include 3- to 8-membered monocyclic nitrogen-containing non-aromatic heterocycles such as aziridine, azetidine, pyrrolidine, pyrroline, piperidine, azepane, morpholine, thiomorpholine, piperazine, oxazolidine, thiazolidine, imidazolidine, oxazoline, thiazoline, imidazoline, pyrazolidine, pyrazoline, tetrahydropyridine, tetrahydropyrimidine, tetrahydrotriazoline, and the like. Among them, azetidine, pyrrolidine, piperidine, piperazine, or morpholine is preferred, and piperidine or piperazine is more preferred.

In the present specification, the "optionally substituted" means unsubstituted or having one or more substituents. Unless otherwise particularly indicated, (1) a halogen atom, (2) a nitro group, (3) a cyano group, (4) a $C_{1-30}$ alkyl group, (5) a halo $C_{1-30}$ alkyl group, (6) a $C_{3-8}$ cycloalkyl group, (7) a $C_{1-30}$ alkoxy group, (8) a halo $C_{1-30}$ alkoxy group, (9) a $C_{6-14}$ aryl group, and the like can be mentioned as the "substituent". Among them, a halogen atom, a cyano group, a $C_{1-6}$ alkyl group, a halo $C_{1-6}$ alkyl group, a $C_{1-6}$ alkoxy group, a halo $C_{1-6}$ alkoxy group, and a phenyl group are preferred, and a halogen atom (e.g., fluorine atom), a $C_{1-4}$ alkyl group (e.g., methyl, ethyl), a $C_{1-4}$ alkoxy group (e.g., methoxy, ethoxy), a halo $C_{1-4}$ alkyl group (e.g., fluoro $C_{1-4}$ alkyl group such as trifluoromethyl, 2,2,2-trifluoroethyl and the like), or a halo $C_{1-4}$ alkoxy group (e.g., fluoro $C_{1-4}$ alkoxy group such as trifluoromethoxy, 2,2,2-trifluoroethoxy, and the like) is more preferred. When plural substituents are present, respective substituents may be the same or different. The above-mentioned substituents may also be further substituted by one or more of a $C_{1-6}$ alkyl group, a $C_{1-6}$ alkoxy group, a halogen atom, a phenyl group, and the like.

In the present specification, specific examples of the "alkali metal ion" include lithium ion, potassium ion, sodium ion, cesium ion, and the like.

In the present specification, specific examples of the "alkaline earth metal ion" include magnesium ion, calcium ion, and the like.

In the present specification, the "hydrocarbon solvent" means solvents including aromatic hydrocarbon solvents and/or aliphatic hydrocarbon solvents. Among them, aliphatic hydrocarbon solvents are preferable from the aspects of odor and toxicity.

In the present specification, examples of the "aromatic hydrocarbon solvent" include benzene, toluene, xylene, and the like.

In the present specification, examples of the "aliphatic hydrocarbon solvent" include n-hexane, isohexane, n-heptane, n-octane, cyclohexane, methylcyclohexane, a mixed solvent thereof, and the like.

In the present specification, the "soluble in hydrocarbon solvent (or aliphatic hydrocarbon solvent)" means that the compound (or composition) of the present invention is dissolved in a solution of a hydrocarbon solvent (or aliphatic hydrocarbon solvent) and the compound (or composition) of the present invention at 25° C. at a concentration of not less than 5 wt % to form a clear homogeneous solution. In addition, the "easily soluble in hydrocarbon solvent (or aliphatic hydrocarbon solvent)" means that the compound (or composition) of the present invention is dissolved in a solution of a hydrocarbon solvent (or aliphatic hydrocarbon solvent) and the compound (or composition) of the present invention at 25° C. at a concentration of not less than 20 wt % (preferably not less than 30 wt %) to form a clear homogeneous solution.

(Compound of the Present Invention)

The compound of the present invention is explained below.

The compound of the present invention is a compound represented by the following formula (1):

(1)

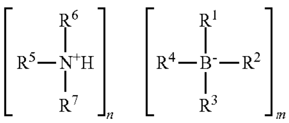

wherein $R^1$, $R^2$, $R^3$, and $R^4$ are each independently a $C_{6-14}$ aryl group substituted by one or more fluorine atoms or one or more fluoro $C_{1-4}$ alkyl groups, $R^5$ is a $C_{1-30}$ alkyl group substituted by one or more substituents selected from the group consisting of a $C_{6-14}$ aryl group substituted by one or more fluorine atoms, and a fluorine atom, $R^6$ and $R^7$ are each independently an optionally substituted $C_{1-30}$ alkyl group, an optionally substituted $C_{3-15}$ cycloalkyl group, or an optionally substituted $C_{6-14}$ aryl group, or $R^6$ and $R^7$ are bonded to each other to form, together with the nitrogen atom bonded thereto, an optionally substituted cyclic group, n is 1, and m is 1 or 2.

Preferred embodiments of the compound represented by the formula (1) (hereinafter to be also referred to as "compound (1)") are explained below.

Each group of compound (1) is explained below.

$R^1$, $R^2$, $R^3$, and $R^4$ are preferably each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 3-phenanthryl group, or a 9-phenanthryl group, each substituted by one or more fluorine atoms or one or more fluoro $C_{1-4}$ alkyl groups (e.g., trifluoromethyl group), more preferably each independently a phenyl group, a 1-naphthyl group, a 2-naphthyl group, or a 4-biphenylyl group, each substituted by one or more fluorine atoms or one or more trifluoromethyl groups, particularly preferably a pentafluorophenyl group, a 2,2',3,3',4',5,5',6,6'-nonafluoro-4-(1,1'-biphenylyl) group, a 2,3,4,5,6,7,8-heptafluoro-1-naphthyl group, or a 1,3,4,5,6,7,8-heptafluoro-2-naphthyl group, wherein all of $R^1$, $R^2$, $R^3$, and $R^4$ are the same.

$R^5$ is preferably a $C_{1-6}$ alkyl group substituted by a phenyl group or a naphthyl group, each of which is substituted by one or more fluorine atoms, or a fluoro $C_{1-6}$ alkyl group, more preferably, a phenylmethyl group substituted by one or more fluorine atoms (e.g., pentafluorophenylmethyl group) or a fluoro $C_{1-6}$ alkyl group, further preferably, a fluoro $C_{1-6}$ alkyl group (e.g., fluoro $C_{1-6}$ alkyl group having fluorine atom(s) at the β-position and/or γ-position such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl, and the like), particularly preferably, a fluoro $C_{1-4}$ alkyl group (e.g., a fluoro $C_{1-4}$ alkyl group having fluorine atom(s) at the β-position such as 2-fluoroethyl, 2,2-difluoroethyl, 2,2,2-trifluoroethyl, pentafluoroethyl, 2,2-difluoropropyl, 2,2,3,3-tetrafluoropropyl, 2,2,3,3,3-pentafluoropropyl, 2,2-difluorobutyl, and the like).

$R^6$ and $R^7$ are preferably each independently a $C_{1-30}$ alkyl group optionally substituted by substituent(s) selected from the group consisting of (1) a $C_{6-14}$ aryl group optionally substituted by halogen atom(s), (2) a halogen atom, and (3) a $C_{1-30}$ alkoxy group; or a $C_{3-8}$ cycloalkyl group optionally substituted by substituent(s) selected from the group consisting of (1) a halogen atom, (2) a $C_{1-30}$ alkyl group, (3) a $C_{1-30}$ alkoxy group, (4) a halo $C_{1-30}$ alkyl group, and (5) a halo $C_{1-30}$ alkoxy group, more preferably, each independently a $C_{1-30}$ alkyl group optionally substituted by substituent(s) selected from the group consisting of (1) a $C_{6-14}$ aryl group optionally substituted by halogen atom(s) (e.g., fluorine atom), (2) a halogen atom, and (3) a $C_{1-30}$ alkoxy group.

In another embodiment of $R^6$ and $R^7$, $R^6$ and $R^7$ are preferably bonded to each other to form, together with the nitrogen atom bonded thereto, an optionally substituted cyclic group derived from a 3- to 8-membered monocyclic nitrogen-containing non-aromatic heterocyclic group, $R^6$ and $R^7$ are more preferably bonded to each other to form, together with the nitrogen atom bonded thereto, a cyclic group derived from an azetidinyl group, a pyrrolidinyl group, a piperidyl group, a piperazinyl group, or a morpholinyl group, each of which is optionally substituted by substituent(s) selected from the group consisting of, (1) a halogen atom (e.g., fluorine atom), (2) a $C_{1-4}$ alkyl group (e.g., methyl, ethyl), (3) a $C_{1-4}$ alkoxy group (e.g., methoxy, ethoxy), (4) a halo $C_{1-4}$ alkyl group (e.g., fluoro $C_{1-4}$ alkyl group such as trifluoromethyl, 2,2,2-trifluoroethyl, and the like), and (5) a halo $C_{1-4}$ alkoxy group, or $R^6$ and $R^7$ are particularly preferably bonded to each other to form, together with the nitrogen atom bonded thereto, a cyclic group derived from a piperidyl group or a piperazinyl group, each of which is optionally substituted by a halogen atom (e.g., fluorine atom), a $C_{1-4}$ alkyl group (e.g., methyl, ethyl), a $C_{1-4}$ alkoxy group (e.g., methoxy, ethoxy), a halo $C_{1-4}$ alkyl group (e.g., fluoro $C_{1-4}$ alkyl group such as trifluoromethyl, 2,2,2-trifluoroethyl, and the like), or a halo $C_{1-4}$ alkoxy group.

The total carbon number of $R^5$, $R^6$, and $R^7$ is preferably not less than 25, more preferably not less than 35.

n is preferably 1.

m is preferably 1 or 2, more preferably 1.

As preferred compound (1), the following compounds can be mentioned.

[Compound (1-1)]

Compound (1) of the aforementioned formula (1), wherein $R^1$, $R^2$, $R^3$, and $R^4$ are each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 3-phenanthryl group, or a 9-phenanthryl group, each of which is substituted by one or more fluorine atoms or one or more fluoro $C_{1-4}$ alkyl groups (e.g., trifluoromethyl group), $R^5$ is a $C_{1-6}$ alkyl group substituted by a phenyl group or a naphthyl group, each of which is substituted by one or more fluorine atoms, or a fluoro $C_{1-6}$ alkyl group (preferably, fluoro $C_{2-4}$ alkyl group having fluorine atom(s) at the β-position and having 3 or more fluorine atoms such as 2,2,2-trifluoroethyl, 2,2,3,3,3-pentafluoropropyl and the like), $R^6$ and $R^7$ are each independently a $C_{1-30}$ alkyl group optionally substituted by substituent(s) selected from the group consisting of (1) a $C_{6-14}$ aryl group optionally substituted by halogen atom(s), (2) a halogen atom, and (3) a $C_{1-30}$ alkoxy group; or a $C_{3-8}$ cycloalkyl group optionally substituted by substituent(s) selected from the group consisting of (1) a halogen atom, (2) a $C_{1-30}$ alkyl group, (3) a $C_{1-30}$ alkoxy group, (4) a halo $C_{1-30}$ alkyl group, and (5) a halo $C_{1-30}$ alkoxy group, n is 1, and m is 1.

[Compound (1-2)]

Compound (1) of the aforementioned formula (1), wherein $R^1$, $R^2$, $R^3$, and $R^4$ are each independently a phenyl group, a 1-naphthyl group, a 2-naphthyl group or a 4-biphenylyl group, each of which is substituted by one or more fluorine atoms or one or more trifluoromethyl groups, $R^5$ is a phenylmethyl group (e.g., pentafluorophenylmethyl group) substituted by one or more fluorine atoms, or a fluoro $C_{1-6}$ alkyl group, further preferably, a fluoro $C_{1-6}$ alkyl group (e.g., fluoro $C_{1-6}$ alkyl group having fluorine atom(s) at the β-position and/or γ-position, such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl, and the like), particularly preferably, a fluoro $C_{2-4}$ alkyl group having fluorine atom(s) at the β-position and having 3 or more fluorine atoms, such as 2,2,2-trifluoroethyl, 2,2,3,3,3-pentafluoropropyl and the like, $R^6$ and $R^7$ are each independently a $C_{1-30}$ alkyl group optionally substituted by substituent(s) selected from the group consisting of (1) a $C_{6-14}$ aryl group optionally substituted by halogen atom(s) (e.g., fluorine atom), (2) a halogen atom, and (3) a $C_{1-30}$ alkoxy group, n is 1, and m is 1.

[Compound (1-3)]

Compound (1) of the aforementioned formula (1), wherein $R^1$, $R^2$, $R^3$, and $R^4$ are all the same and are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups, $R^5$ is a fluoro $C_{1-6}$ alkyl group (e.g., fluoro $C_{1-6}$ alkyl group having fluorine atom(s) at the β-position and/or γ-position such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl, and the like), $R^6$ and $R^7$ are each independently a $C_{1-30}$ alkyl group optionally substituted by substituent(s) selected from the group consisting of (1) a $C_{6-14}$ aryl group optionally substituted by halogen atom(s) (e.g., fluorine atom), (2) a halogen atom, and (3) a $C_{1-30}$ alkoxy group, n is 1, and m is 1.

[Compound (1-4)]

Compound (1) of the aforementioned formula (1), wherein $R^1$, $R^2$, $R^3$, and $R^4$ are all the same and are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups, $R^5$ is a fluoro $C_{1-4}$ alkyl group (e.g., fluoro $C_{1-4}$ alkyl groups having fluorine atom(s) at the β-position such as 2-fluoroethyl, 2,2-difluoroethyl, 2,2,2-trifluoroethyl, pentafluoroethyl, 2,2-difluoropropyl, 2,2,3,3-tetrafluoropropyl, 2,2,3,3,3-pentafluoropropyl, 2,2-difluorobutyl, and the like, among which a fluoro $C_{2-4}$ alkyl group having fluorine atom(s) at the β-position and having 3 or more fluorine atoms such as 2,2,2-trifluoroethyl, 2,2,3,3,3-pentafluoropropyl, and the like is preferred), $R^6$ and $R^7$ are each independently a $C_{1-30}$ alkyl group optionally substituted by substituent(s) selected from the group consisting of (1) a $C_{6-14}$ aryl group optionally substituted by halogen atom(s) (e.g., fluorine atom), (2) a halogen atom, and (3) a $C_{1-30}$ alkoxy group, n is 1, and m is 1.

[Compound (1-5)]

Compound (1) of the aforementioned formula (1), wherein $R^1$, $R^2$, $R^3$, and $R^4$ are each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 3-phenanthryl group, or a 9-phenanthryl group, substituted by one or more fluorine atoms or one or more fluoro $C_{1-4}$ alkyl groups (e.g., trifluoromethyl group), $R^5$ is a $C_{1-6}$ alkyl group substituted by a phenyl group or a naphthyl group, each of which is substituted by one or more fluorine atoms, or a fluoro $C_{1-6}$ alkyl group (preferably, fluoro $C_{2-4}$ alkyl group having fluorine atom(s) at the β-position and having 3 or more fluorine atoms such as 2,2,2-trifluoroethyl, 2,2,3,3,3-pentafluoropropyl, and the like), $R^6$ and $R^7$ are bonded to each other to form, together with the nitrogen atom bonded thereto, an optionally substituted cyclic group derived from a 3- to 8-membered monocyclic nitrogen-containing non-aromatic heterocyclic group, n is 1, and m is 1 or 2.

[Compound (1-6)]

Compound (1) of the aforementioned formula (1), wherein $R^1$, $R^2$, $R^3$, and $R^4$ are each independently a phenyl group, a 1-naphthyl group, a 2-naphthyl group, or a 4-biphenylyl group substituted by one or more fluorine atoms or one or more trifluoromethyl groups, $R^5$ is a phenylmethyl group substituted by one or more fluorine atoms (e.g., pentafluorophenylmethyl group) or a fluoro $C_{1-6}$ alkyl group, further preferably, a fluoro $C_{1-6}$ alkyl group (e.g., fluoro $C_{1-6}$ alkyl group having fluorine atom(s) at the β-position and/or γ-position such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl, and the like, among which a fluoro $C_{2-4}$ alkyl group having fluorine atom(s) at the β-position and having 3 or more fluorine atoms such as 2,2,2-trifluoroethyl, 2,2,3,3,3-pentafluoropropyl and the like is preferred), $R^6$ and $R^7$ are bonded to each other to form, together with the nitrogen atom bonded thereto, a cyclic group derived from an azetidinyl group, a pyrrolidinyl group, a piperidyl group, a piperazinyl group, or a morpholinyl group, each of which is optionally substituted by substituent(s) selected from the group consisting of (1) a halogen atom (e.g., fluorine atom), (2) a $C_{1-4}$ alkyl group (e.g., methyl, ethyl), (3) a $C_{1-4}$ alkoxy group (e.g., methoxy, ethoxy), (4) a halo $C_{1-4}$ alkyl group (e.g., fluoro $C_{1-4}$ alkyl group such as trifluoromethyl, 2,2,2-trifluoroethyl, and the like), and (5) a halo $C_{1-4}$ alkoxy group, n is 1, and m is 1 or 2.

[Compound (1-7)]

Compound (1) of the aforementioned formula (1), wherein $R^1$, $R^2$, $R^3$, and $R^4$ are all the same and are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups, $R^5$ is a fluoro $C_{1-6}$ alkyl group (e.g., fluoro $C_{1-6}$ alkyl group having fluorine atom(s) at the β-position and/or γ-position such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl, and the like, among which fluoro $C_{2-4}$ alkyl group having fluorine atom(s) at the β-position and having 3 or more fluorine atoms such as 2,2,2-trifluoroethyl, 2,2,3,3,3-pentafluoropropyl, and the like are preferred), $R^6$ and $R^7$ are bonded to each other to form, together with the nitrogen atom bonded thereto, a cyclic group derived from a piperidyl group or a piperazinyl group, each of which is optionally substituted by substituent(s) selected from the group consisting of, (1) a halogen atom (e.g., fluorine atom), (2) a $C_{1-4}$ alkyl group (e.g., methyl, ethyl), (3) a $C_{1-4}$ alkoxy group (e.g., methoxy, ethoxy), (4) a halo $C_{1-4}$ alkyl group (e.g., fluoro $C_{1-4}$ alkyl group such as trifluoromethyl, 2,2,2-trifluoroethyl, and the like), and (5) a halo $C_{1-4}$ alkoxy group, n is 1, and m is 1 or 2.

[Compound (1-8)]

Compound (1) of the aforementioned formula (1), wherein $R^1$, $R^2$, $R^3$, and $R^4$ are all the same and are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups, $R^5$ is a fluoro $C_{1-4}$ alkyl group (e.g., fluoro $C_{1-4}$ alkyl group having fluorine atom(s) at the β-position such as 2-fluoroethyl, 2,2-difluoroethyl, 2,2,2-trifluoroethyl, pentafluoroethyl, 2,2-difluoropropyl, 2,2,3,3-tetrafluoropropyl, 2,2,3,3,3-pentafluoropropyl, 2,2-difluorobutyl, and the like, among which fluoro $C_{2-4}$ alkyl group having fluorine atom(s) at the β-position and having 3 or more fluorine atoms such as 2,2,2-trifluoroethyl, 2,2,3,3,3-pentafluoropropyl, and the like are preferred), $R^6$ and $R^7$ are bonded to each other to form, together with the nitrogen atom bonded thereto, a cyclic group derived from a piperidyl group optionally substituted by substituent(s) selected from the group consisting of (1) a halogen atom (e.g., fluorine atom), (2) a $C_{1-4}$ alkyl group (e.g., methyl, ethyl), (3) a $C_{1-4}$ alkoxy group (e.g., methoxy, ethoxy), (4) a halo $C_{1-4}$ alkyl group (e.g., fluoro $C_{1-4}$ alkyl group such as trifluoromethyl, 2,2,2-trifluoroethyl, and the like), and (5) a halo $C_{1-4}$ alkoxy group, n is 1, and m is 1.

Specific preferable examples of compound (1) include, for example, the compounds of the below-mentioned Examples 1, 4 to 21, 23, and 25, and the like.

(Composition of the Present Invention)

The composition of the present invention is explained below.

The composition of the present invention is a composition containing the aforementioned compound (1) (the compound of the present invention), and a compound represented by the following formula (2):

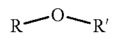

(2)

wherein

R and R' are each independently an optionally substituted $C_{1-30}$ alkyl group, an optionally substituted $C_{3-15}$ cycloalkyl group, or an optionally substituted $C_{6-14}$ aryl group (hereinafter to be also referred to as "compound (2)").

The composition containing compound (1) and compound (2) is not particularly limited as long as it contains the both compounds, and may include a compound in which compound (2) is coordinated to compound (1) to form a complex. The composition of the present invention is preferably a composition including a complex formed by compound (1) and compound (2).

Preferred embodiments of compound (2) are explained below.

Each group of compound (2) is explained below.

R and R' are each independently an optionally substituted $C_{1-30}$ alkyl group, an optionally substituted $C_{3-15}$ cycloalkyl group, or an optionally substituted $C_{6-14}$ aryl group, preferably, each independently a $C_{1-30}$ alkyl group optionally substituted by substituent(s) selected from the group consisting of (1) a halogen atom, (2) a $C_{1-30}$ alkoxy group, and (3) a halo $C_{1-30}$ alkoxy group;

a $C_{3-15}$ cycloalkyl group optionally substituted by substituent(s) selected from the group consisting of (1) a halogen atom, (2) a $C_{1-30}$ alkyl group, (3) a $C_{1-30}$ alkoxy group, (4) a halo $C_{1-30}$ alkyl group, and (5) a halo $C_{1-30}$ alkoxy group; or a $C_{6-14}$ aryl group optionally substituted by substituent(s) selected from the group consisting of (1) a halogen atom, (2) a $C_{1-30}$ alkyl group, (3) a $C_{1-30}$ alkoxy group, (4) a halo $C_{1-30}$ alkyl group, and (5) a halo $C_{1-30}$ alkoxy group, more preferably, each independently a $C_{1-30}$ alkyl group; a $C_{3-8}$ cycloalkyl group (e.g., cyclopentyl, cyclohexyl, etc.); or a phenyl group optionally substituted by substituent(s) selected from the group consisting of (1) a halogen atom, (2) a $C_{1-6}$ alkyl group, (3) a $C_{1-6}$ alkoxy group, (4) a halo $C_{1-6}$ alkyl group, and (5) a halo $C_{1-6}$ alkoxy group, further preferably, each independently a $C_{1-30}$ alkyl group (preferably, $C_{1-18}$ alkyl group such as methyl, butyl, hexyl, octyl, decyl, dodecyl, tetradecyl, hexadecyl, octadecyl, and the like).

Specific preferable examples of compound (2) include dibutyl ether, dihexyl ether, dioctyl ether, dodecyl ether, didodecyl ether, ditetradecyl ether, dihexadecyl ether, dioctadecyl ether, cyclopentyl methyl ether, diphenyl ether, phenyl octadecyl ether, and the like.

In the composition of the present invention, the content of compound (2) with respect to 1 mol of compound (1) is preferably 0.01 to 10 mol, more preferably 0.1 to 3 mol.

Specific preferable examples of the composition of the present invention include the compositions of the below-mentioned Examples 2, 3, 24, 26 to 34, and the like.

Another embodiment of the composition of the present invention is a composition containing the aforementioned compound (1) (the compound of the present invention), and a compound represented by the following formula (3):

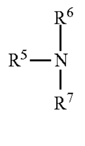

(3)

wherein $R^5$, $R^6$, and $R^7$ are as defined above (hereinafter to be also referred to as "compound (3)")

(in this composition, compound (3) is an amine compound deprotonated from the cation constituting the aforementioned compound (1)).

The preferred embodiment of compound (3) is the same as the preferred embodiment of each group ($R^5$, $R^6$, and R') in compound (1), except that $R^6$ and $R^7$ are deprotonated when they bond with each other to form a cyclic group together with the nitrogen atom bonded thereto.

As preferred compound (3), the following compounds can be mentioned.

[Compound (3-1)]

Compound (3) wherein, in the aforementioned formula (3), $R^5$ is a $C_{1-6}$ alkyl group substituted by a phenyl group or a naphthyl group, each of which is substituted by one or more fluorine atoms, or a fluoro $C_{1-6}$ alkyl group (preferably, fluoro $C_{2-4}$ alkyl group having fluorine atom(s) at the β-position and having 3 or more fluorine atoms such as 2,2,2-trifluoroethyl, 2,2,3,3,3-pentafluoropropyl and the like), and $R^6$ and $R^7$ are each independently a $C_{1-30}$ alkyl group optionally substituted by substituent(s) selected from the group consisting of (1) a $C_{6-14}$ aryl group optionally substituted by halogen atom(s), (2) a halogen atom, and (3) a $C_{1-30}$ alkoxy group; or a $C_{3-8}$ cycloalkyl group optionally substituted by substituent(s) selected from the group consisting of (1) a halogen atom, (2) a $C_{1-30}$ alkyl group, (3) a $C_{1-30}$ alkoxy group, (4) a halo $C_{1-30}$ alkyl group, and (5) a halo $C_{1-30}$ alkoxy group.

[Compound (3-2)]

Compound (3) wherein, in the aforementioned formula (3), $R^5$ is a phenylmethyl group (e.g., pentafluorophenylmethyl group) or a fluoro $C_{1-6}$ alkyl group, each of which is substituted by one or more fluorine atoms, further preferably, a fluoro $C_{1-6}$ alkyl group (e.g., fluoro $C_{1-6}$ alkyl group having fluorine atom(s) at the β-position and/or γ-position such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl, and the like, among which, preferably a fluoro $C_{2-4}$ alkyl group having fluorine atom(s) at the β-position and having 3 or more fluorine atoms such as 2,2,2-trifluoroethyl, 2,2,3,3,3-pentafluoropropyl and the like), and $R^6$ and $R^7$ are each independently a $C_{1-30}$ alkyl group optionally substituted by substituent(s) selected from the group consisting of (1) a $C_{6-14}$ aryl group optionally substituted by halogen atom(s), (2) a halogen atom, and (3) a $C_{1-30}$ alkoxy group.

[Compound (3-3)]

Compound (3) wherein, in the aforementioned formula (3), $R^5$ is a fluoro $C_{1-6}$ alkyl group (e.g., fluoro $C_{1-6}$ alkyl group having fluorine atom(s) at the β-position and/or γ-position such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl, and the like), among which, preferably a fluoro $C_{2-4}$ alkyl group having fluorine atom(s) at the β-position and having 3 or more fluorine atoms such as 2,2,2-trifluoroethyl, 2,2,3,3,3-pentafluoropropyl and the like), and $R^6$ and $R^7$ are each independently a $C_{1-30}$ alkyl group optionally substituted by substituent(s) selected from the group consisting of (1) a $C_{6-14}$ aryl group optionally substituted by halogen atom(s) (e.g., fluorine atom), (2) a halogen atom, and (3) a $C_{1-30}$ alkoxy group.

[Compound (3-4)]

Compound (3) wherein, in the aforementioned formula (3), $R^5$ is a fluoro $C_{1-4}$ alkyl group (e.g., fluoro $C_{1-4}$ alkyl group having fluorine atom(s) at the ß-position such as 2-fluoroethyl, 2,2-difluoroethyl, 2,2,2-trifluoroethyl, pentafluoroethyl, 2,2-difluoropropyl, 2,2,3,3-tetrafluoropropyl, 2,2,3,3,3-pentafluoropropyl, 2,2-difluorobutyl, and the like, among which a fluoro $C_{2-4}$ alkyl group having fluorine atom(s) at the β-position and having 3 or more fluorine atoms such as 2,2,2-trifluoroethyl, 2,2,3,3,3-pentafluoropropyl, and the like is preferred), and $R^6$ and $R^7$ are each independently a $C_{1-30}$ alkyl group optionally substituted by substituent(s) selected from the group consisting of a $C_{6-14}$ aryl group optionally substituted by halogen atom(s) (e.g., fluorine atom), a halogen atom, and a $C_{1-30}$ alkoxy group.

[Compound (3-5)]

Compound (3) wherein, in the aforementioned formula (3), $R^5$ is a $C_{1-6}$ alkyl group substituted by a phenyl group or a naphthyl group, each of which is substituted by one or more fluorine atoms, or a fluoro $C_{1-6}$ alkyl group (preferably, fluoro $C_{2-4}$ alkyl group having fluorine atom(s) at the β-position and having 3 or more fluorine atoms such as 2,2,2-trifluoroethyl, 2,2,3,3,3-pentafluoropropyl and the like), and $R^6$ and $R^7$ are bonded to each other to form, together with the nitrogen atom bonded thereto, an optionally substituted 3 to 8-membered monocyclic nitrogen-containing non-aromatic heterocycle.

[Compound (3-6)]

Compound (3) wherein, in the aforementioned formula (3), $R^5$ is a phenylmethyl group substituted by one or more fluorine atoms (e.g., pentafluorophenylmethyl group) or a fluoro $C_{1-6}$ alkyl group, further preferably, a fluoro $C_{1-6}$ alkyl group (e.g., fluoro $C_{1-6}$ alkyl group having fluorine atom(s) at the β-position and/or γ-position such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl, and the like), among which, preferably a fluoro $C_{2-4}$ alkyl group having fluorine atom(s) at the β-position and having 3 or more fluorine atoms such as 2,2,2-trifluoroethyl, 2,2,3,3,3-pentafluoropropyl and the like), and $R^6$ and $R^7$ are bonded to each other to form, together with the nitrogen atom bonded thereto, azetidine, pyrrolidine, piperidine, piperazine, or morpholine, each of which is optionally substituted by substituent(s) selected from the group consisting of (1) a halogen atom (e.g., fluorine atom), (2) a $C_{1-4}$ alkyl group (e.g., methyl, ethyl), (3) a $C_{1-4}$ alkoxy group (e.g., methoxy, ethoxy), (4) a halo $C_{1-4}$ alkyl group (e.g., fluoro $C_{1-4}$ alkyl group such as trifluoromethyl, 2,2,2-trifluoroethyl, and the like), and (5) a halo $C_{1-4}$ alkoxy group.

[Compound (3-7)]

Compound (3) wherein, in the aforementioned formula (3), $R^5$ is a fluoro $C_{1-6}$ alkyl group (e.g., fluoro $C_{1-6}$ alkyl group having fluorine atom(s) at the β-position and/or γ-position such as 2-fluoroethyl, 2,2-difluoroethyl, 2,2,2-trifluoroethyl, pentafluoroethyl, 2,2-difluoropropyl, 2,2,3,3-tetrafluoropropyl, 3,3,3-trifluoropropyl, 2,2,3,3,3-pentafluoropropyl, 2,2-difluorobutyl, 2,2-difluoropentyl, 2,2-difluorohexyl, and the like, among which, preferably a fluoro $C_{2-4}$ alkyl group having fluorine atom(s) at the β-position and having 3 or more fluorine atoms such as 2,2,2-trifluoroethyl, 2,2,3,3,3-pentafluoropropyl and the like), and $R^6$ and $R^7$ are bonded to each other to form, together with the nitrogen atom bonded thereto, piperidine or piperazine, each of which is optionally substituted by substituent(s) selected from the group consisting of (1) a halogen atom (e.g., fluorine atom), (2) a $C_{1-4}$ alkyl group (e.g., methyl, ethyl), (3) a $C_{1-4}$ alkoxy group (e.g., methoxy, ethoxy), (4) a halo $C_{1-4}$ alkyl group (e.g., fluoro $C_{1-4}$ alkyl group such as trifluoromethyl, 2,2,2-trifluoroethyl, and the like), and (5) a halo $C_{1-4}$ alkoxy group.

[Compound (3-8)]

Compound (3) wherein, in the aforementioned formula (3), $R^5$ is a fluoro $C_{1-4}$ alkyl group (e.g., a fluoro $C_{1-4}$ alkyl group having fluorine atom(s) at the β-position such as 2-fluoroethyl, 2,2-difluoroethyl, 2,2,2-trifluoroethyl, pentafluoroethyl, 2,2-difluoropropyl, 2,2,3,3-tetrafluoropropyl, 2,2,3,3,3-pentafluoropropyl, 2,2-difluorobutyl, and the like, among which, preferably a fluoro $C_{2-4}$ alkyl group having fluorine atom(s) at the β-position and having 3 or more fluorine atoms such as 2,2,2-trifluoroethyl, 2,2,3,3,3-pentafluoropropyl, and the like), and $R^6$ and $R^7$ are bonded to each other to form, together with the nitrogen atom bonded thereto, piperidine optionally substituted by substituent(s) selected from the group consisting of (1) a halogen atom (e.g., fluorine atom), (2) a $C_{1-4}$ alkyl group (e.g., methyl, ethyl), (3) a $C_{1-4}$ alkoxy group (e.g., methoxy, ethoxy), (4) a halo $C_{1-4}$ alkyl group (e.g., fluoro $C_{1-4}$ alkyl group such as trifluoromethyl, 2,2,2-trifluoroethyl, and the like) and (5) a halo $C_{1-4}$ alkoxy group.

Specific preferable examples of compound (3) include fluorine-containing alkylamine, fluorine-containing alkylcyclic amine, and the like used for synthesizing the compounds of the below-mentioned Examples 1, 4 to 21.

In the composition of the present invention including compound (1) and compound (3), the content of compound (3) with respect to 1 mol of compound (1) is preferably 0.01 to 10 mol, more preferably 0.5 to 3 mol.

Specific preferable examples of the composition of the present invention including compound (1) and compound (3) include the composition of the below-mentioned Example 22 and the like.

The composition of the present invention containing compound (1) and compound (3) may further contain the aforementioned compound (2) in addition to compound (1) and compound (3).

A preferred embodiment of compound (2) that may be further contained is the same as the preferred embodiment of each group (R and R') in the aforementioned compound (2) and specific preferable examples thereof. In the composition of the present invention containing compound (1), compound (2), and compound (3), the content of each of compound (2) and compound (3) with respect to 1 mol of compound (1) is the same as that mentioned above.

In the compound or composition of the present invention, when the total carbon number of $R^5$, $R^6$, and $R^7$ in the aforementioned formula (1) is not less than 25, it is soluble in aliphatic hydrocarbon solvents at room temperature (15 to 30° C.). In contrast, conventionally-known borate-type compounds (e.g., hydrogenated tetrakis(pentafluorophenyl)borate, hydrogenated tetrakis(pentafluorophenyl)borate diethyl ether complex, lithium tetrakis(pentafluorophenyl)borate, etc.) are insoluble in aliphatic hydrocarbon solvents such as n-hexane and the like. Thus, known borate compounds are generally used for polymerization reactions as a solution of aromatic hydrocarbon solvents. As a result, removal of the contaminating aromatic hydrocarbon solvent becomes necessary, and there are problems such as a large commercial cost associated with an increase in the number of steps. In some cases, it is used in the polymerization reaction as a suspension of an aliphatic hydrocarbon solvent. However, there are problems such as poor operability due to being suspended, the need for an excessive amount, and the like. Therefore, the compound or composition of the present invention that is soluble in aliphatic hydrocarbon solvents is particularly useful as a co-catalyst for homogeneous polymerization reactions of olefin, diene, and acetylene, using hydrocarbon solvents (particularly, aliphatic hydrocarbon solvents).

(Production Method of the Compound of the Present Invention)

The production method of the compound (or composition) of the present invention (hereinafter to be also referred to as "the production method of the present invention") is explained below.

The production method of the compound (or composition) of the present invention is not particularly limited, and it can be produced according to the methods described in, for example, the following Production Methods 1 to 3, or the below-mentioned Production Examples or Examples. Particularly, it is possible to obtain the compound (or composition) of the present invention in a simple operation at a low cost and in a high yield as compared with the conventional methods, by producing a fluorine-containing alkylamine by the following production method. Thus, the production method can be an industrial production method.

(Production Method 1)

Production Method 1 includes a step of obtaining compound (7) by reacting dialkylamine compound (5) with fluoroalkylcarboxylic anhydride (6) in the presence of a base in a solvent that does not affect the reaction (step 1), a step of converting compound (7) to compound (3a) by reducing with a reducing agent in a solvent that does not affect the reaction (step 2), and a step of obtaining compound (1a) (the compound of the present invention) by reacting compound (3a) with compound (4) in a solvent that does not affect the reaction and in the presence of an acid (step 3).

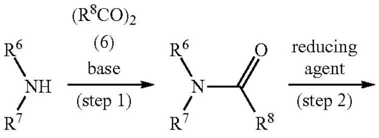

(5) (7)

-continued

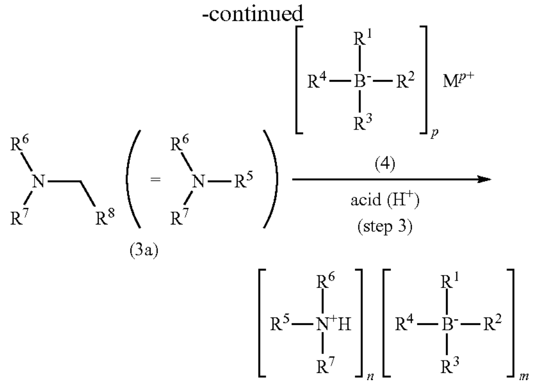

(3a) (1a)

wherein $R^8$ is a $C_{1-29}$ alkyl group substituted by one or more substituents selected from the group consisting of a $C_{6-14}$ aryl group substituted by one or more fluorine atoms and a fluorine atom, and other each symbol is as defined above.

(Step 1)

The solvent used in this step includes, for example, hydrocarbon solvents such as toluene, n-hexane, isohexane, n-heptane, n-octane, cyclohexane, methylcyclohexane, and the like; ethers such as diethyl ether, tetrahydrofuran, and the like; halogen solvents such as chloroform, dichloromethane, and the like; and a mixed solvent thereof, and a toluene-tetrahydrofuran mixed solvent is particularly preferred.

The amount of compound (6) to be used is generally 1 to 3 mol, preferably 1 to 2 mol, more preferably 1.2 mol, per 1 mol of compound (5).

The base used in this step includes, for example, organic bases such as triethylamine, N,N-diisopropylethylamine, pyridine, 2,6-lutidine, and the like, and among them, triethylamine is preferred.

The amount of the base to be used is generally 1 to 3 mol, preferably 1 to 2 mol, more preferably 1.2 mol, per 1 mol of compound (5).

The reaction temperature is generally 0° C. to 40° C., preferably 10° C. to 35° C., more preferably room temperature (15° C. to 30° C.), and the reaction time is generally about 10 min to 10 hr, preferably about 30 min to 2 hr.

In Production Method 1, compound (7) prepared as mentioned above can be directly used in step 2.

(Step 2)

The solvent used in this step is not particularly limited and includes, for example, ethers such as triglyme, tetrahydrofuran, tetrahydropyran, dioxane, and the like, and among them, tetrahydrofuran is preferred.

The reducing agent used in this step includes, for example, boron hydride, aluminum hydride, and the like. Specific examples of the reducing agent include, but are not particularly limited to, sodium borohydride, lithium borohydride, lithium aluminum hydride, borane-tetrahydrofuran m complex, borane-dimethylsulfide complex, sodium borohydride/iodine, sodium borohydride/trifluoroacetic acid, and the like, and among them, boron hydrides such as borane-tetrahydrofuran complex, borane-dimethylsulfide complex, sodium borohydride/iodine, sodium borohydride/trifluoroacetic acid, and the like are preferred.

The amount of the reducing agent such as borane-tetrahydrofuran complex, borane-dimethylsulfide complex, sodium borohydride/iodine, sodium borohydride/trifluoroacetic acid, and the like to be used is generally 2 to 10 mol, preferably 2 to 3 mol, per 1 mol of compound (7).

The reaction temperature is generally the refluxing temperature of the solvent to be used, preferably 40° C. to 80° C.

The reaction time is generally about 30 min to 10 hr, preferably about 1 to 4 hr.

(Step 3)

The solvent used in this step is not particularly limited and includes, for example, halogenated hydrocarbons such as dichloromethane, chloroform, dichloroethane, carbon tetrachloride, trichloroethylene, and the like and hydrocarbon solvents such as toluene, n-hexane, isohexane, n-heptane, n-octane, cyclohexane, methylcyclohexane, and the like, and dichloromethane, chloroform, n-hexane, isohexane, n-heptane, cyclohexane, methylcyclohexane, and the like are preferred, and among them, dichloroethane, chloroform, n-hexane, isohexane, n-heptane, or methylcyclohexane is particularly preferred.

Examples of the acid used in this step include protic acids such as hydrogen bromide, hydrogen chloride, hydrogen iodide, and the like, and among them, hydrogen chloride is preferred. As hydrogen chloride, a commercially available product (1.0 M hydrogen chloride-diethyl ether solution or hydrochloric acid) can be directly used.

The amount of the acid to be used is generally 1 to 5 mol, preferably 1 to 2 mol, per 1 mol of compound (3a).

Compound (4) used in this step is not particularly limited, and a commercially available product or purified product may also be used. In addition, one prepared by a method known per se may also be used. Specific examples of compound (4) include lithium tetrakis(pentafluorophenyl) borate, potassium tetrakis(pentafluorophenyl)borate, lithium tetrakis(heptafluoronaphthyl)borate, potassium tetrakis(heptafluoronaphthyl)borate, chloro magnesium tetrakis(pentafluorophenyl)borate, chloro magnesium tetrakis(heptafluoronaphthyl)borate, bromo magnesium tetrakis (pentafluorophenyl)borate, bromo magnesium tetrakis (heptafluoronaphthyl)borate, lithium tetrakis (nonafluorobiphenyl)borate, potassium tetrakis (nonafluorobiphenyl)borate, chloro magnesium tetrakis (nonafluorobiphenylyl)borate, bromo magnesium tetrakis (nonafluorobiphenyl)borate, tri-diethyl ether complex of lithium tetrakis(pentafluorophenyl)borate, mono-diethyl ether complex of lithium tetrakis(pentafluorophenyl)borate, and the like.

The amount of compound (4) to be used is generally 1 to 1.5 mol, preferably 1 mol, per 1 mol of compound (3a).

The reaction temperature is generally 0° C. to 80° C., preferably 15° C. to 60° C., and the reaction time is generally about 10 min to 10 hr, preferably about 1 to 3 hr.

(Production Method 2)

Production Method 2 is a method of obtaining a composition containing compound (1a) and compound (2) (the composition of the present invention) by performing the reaction of the aforementioned Production Method 1, step 3, in the presence of a compound represented by the formula (2):

(2)

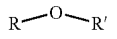

wherein each symbol is as defined above (compound (2)).

The method can be performed in the same manner as in the aforementioned Production Method 1, step 3, except that compound (2) is added.

The amount of compound (2) to be used is generally 0.01 to 10 mol, preferably 0.1 to 3 mol, per 1 mol of compound (4).

(Production Method 3)

Production Method 3 is a method of obtaining a composition containing compound (1a) and compound (3a) (the composition of the present invention) by using an excess amount of compound (3a) in the reaction of the aforementioned Production Method 1, step 3. The method can be performed in the same manner as in the aforementioned Production Method 1, step 3, except that an excess amount of compound (3a) is used.

The amount of compound (3a) to be used is generally 1.01 to 11 mol, preferably 1.1 to 4 mol, per 1 mol of compound (4).

The compound of the present invention (compound (1)) or the composition of the present invention is a compound or composition derived from fluorine-containing alkylamine, and is substantially free of compounds that can be catalyst poison, such as amine compounds with high basicity and high nucleophilicity. Therefore, it is useful as a co-catalyst for the polymerization of olefin, diene, and acetylene.

The present invention encompasses production methods of polymers, including polymerizing at least one kind of monomer selected from the group consisting of olefin, diene, and acetylene by using the compound of the present invention (compound (1)) or the composition of the present invention as a co-catalyst.

Production of a polymer by using the compound of the present invention (compound (1)) (or composition) as a co-catalyst can be specifically performed according to, for example, the method described in the below-mentioned Experimental Example.

Example

The present invention is specifically explained in detail in the following by referring to Examples, Production Examples, and Experimental Example; however, the present invention is not limited to those Examples and the like. % means mol/mol % for yield and wt % for others unless particularly indicated. The room temperature refers to a temperature of from 15° C. to 30° C. unless particularly indicated.

Unless otherwise specified, the solvents and reagents used in the following Examples were purchased from vendors such as Tokyo Chemical Industry Co., Ltd., FUJIFILM Wako Pure Chemical Corporation, Junsei Chemical Co., Ltd., KANTO CHEMICAL CO., INC., Combi-Blocks, Inc, and the like. In addition, the deuterated solvents used for NMR measurement were purchased from Cambridge Isotope Laboratories, Inc.

For the analysis, the following instrument was used.

$^{1}$H-NMR and $^{19}$F-NMR: 400YH manufactured by JEOL Ltd. (JEOL).

Production Example 1

Synthesis of N,N-dioctadecyl-2,2,2-trifluoroacetamide

N,N-Dioctadecylamine (2.0 g, 3.8 mmol) and triethylamine (0.5 g, 5.0 mmol) were dissolved in tetrahydrofuran (10 mL), and trifluoroacetic anhydride (1.0 g, 4.8 mmol) was added at room temperature. The mixture was stirred at room temperature for 1 hr, water was added, and the mixture was extracted with ethyl acetate. The organic layer was washed with 1 M hydrochloric acid and saturated brine, dried over anhydrous magnesium sulfate, and concentrated under reduced pressure. The residue was purified by column chromatography (n-hexane/ethyl acetate=100/0-95/5) to give the title compound (1.87 g, 79%).

$^1$H NMR ($CDCl_3$) δ: 0.89 (6H, t), 1.26-1.43 (60H, m), 1.56-1.59 (4H, m), 3.30-3.37 (4H, m);

$^{19}$F NMR ($CDCl_3$) δ: −70.1 (3F, s).

Production Example 2

Synthesis of N,N-dioctadecyl-2,2,2-trifluoroethylamine

N,N-Dioctadecyl-2,2,2-trifluoroacetamide (1.0 g, 1.6 mmol) obtained in Production Example 1 was dissolved in tetrahydrofuran (10 mL), 1 M borane-tetrahydrofuran complex solution in tetrahydrofuran (5 mL) was added, and the mixture was refluxed for 3 hr. The mixture was ice-cooled, water was carefully added dropwise thereto, and the mixture was extracted with ethyl acetate. The organic layer was washed with saturated brine, dried over anhydrous magnesium sulfate, and concentrated under reduced pressure to give the title compound (0.87 g, 88%).

$^1$H NMR ($CDCl_3$) δ: 0.88 (6H, t), 1.25-1.40 (60H, m), 1.42-1.44 (4H, m), 2.56 (4H, t), 3.00 (2H, q);

$^{19}$F NMR ($CDCl_3$) δ: −71.3 (3F, t).

Production Example 3

Synthesis of N,N-dioctadecyl-2,2,2-trifluoroethylamine hydrochloride

N,N-Dioctadecyl-2,2,2-trifluoroethylamine (1.0 g, 1.7 mmol) obtained in Production Example 2 was dissolved in n-hexane (10 mL), 1.0 M hydrogen chloride-diethyl ether solution (10 mL) was added, and the mixture was stirred at room temperature for 3 hr. The precipitate was collected by filtration, washed with n-hexane, and dried under reduced pressure to give the title compound (0.987 g, 93%).

$^1$H NMR ($CDCl_3$) δ: 0.88 (6H, t), 1.19-1.40 (60H, m), 1.93 (4H, br s), 3.15 (4H, br s), 3.77 (2H, q);

$^{19}$F NMR ($CDCl_3$) δ: −63.4 (3F, t).

Example 1

Synthesis of N,N-dioctadecyl-2,2,2-trifluoroethylammonium tetrakis(pentafluorophenyl)borate N,N-Dioctadecyl-2,2,2-trifluoroethylamine hydrochloride (0.32 g, 0.5 mmol) obtained in Production Example 3 was dissolved in chloroform (30 mL), lithium tetrakis(pentafluorophenyl)borate tri-diethyl ether complex (0.45 g, 0.5 mmol) was added, and the mixture was stirred at room temperature for 1 hr. Insoluble material was removed by filtration, and the filtrate was concentrated under reduced pressure. The residue was dried under reduced pressure at 45° C. to give the title compound (0.62 g, 97%).

$^1$H NMR ($CDCl_3$) δ: 0.88 (6H, t), 1.19-1.40 (60H, m), 1.94 (4H, br s), 3.15 (4H, br s), 3.77 (2H, q);

$^{19}$F NMR ($CDCl_3$) δ: −66.7 (3F, t), −134.1 (8H, m), −163.2 (4H, m), −1675.5 (8H, m).

Example 2

Synthesis of composition containing N,N-dioctadecyl-2,2,2-trifluoroethylammonium tetrakis(pentafluorophenyl)borate and ditetradecyl ether N,N-Dioctadecyl-2,2,2-trifluoroethylammonium tetrakis (pentafluorophenyl)borate (0.30 g, 0.22 mmol) obtained in Example 1 was mixed with ditetradecyl ether (0.09 g, 0.22 mmol) to give the title composition.

$^1$H NMR ($CDCl_3$) δ: 0.85-0.90 (12H, m), 1.20-1.33 (104H, m), 1.52-1.68 (8H, m), 3.14-3.18 (4H, m), 3.40 (4H, t), 3.62 (2H, q);

$^{19}$F NMR ($CDCl_3$) δ: −66.8 (3F, br s), −134.0 (8F, m), −163.2 (4F, t), −167.5 (8F, m).

n-Hexane was added to the composition obtained in Example 2 to prepare a 20 wt % n-hexane solution thereof, and the solution was confirmed to be a homogeneous solution.

Isohexane was added to the composition obtained in Example 2 to prepare a 20 wt % isohexane solution thereof, and the solution was confirmed to be a homogeneous solution.

n-Heptane was added to the composition obtained in Example 2 to prepare a 20 wt % n-heptane solution thereof, and the solution was confirmed to be a homogeneous solution.

ISOPAR E (registered trade mark) was added to the composition obtained in Example 2 to prepare a 20 wt % ISOPAR E (registered trade mark) solution thereof, and the solution was confirmed to be a homogeneous solution.

Cyclohexane was added to the composition obtained in Example 2 to prepare a 20 wt % cyclohexane solution thereof, and the solution was confirmed to be a homogeneous solution.

Methylcyclohexane was added to the composition obtained in Example 2 to prepare a 20 wt % methylcyclohexane solution thereof, and the solution was confirmed to be a homogeneous solution.

Example 3

Synthesis of composition containing N,N-dioctadecyl-2,2,2-trifluoroethylammonium tetrakis(pentafluorophenyl)borate and dibutyl ether N,N-Dioctadecyl-2,2,2-trifluoroethylammonium tetrakis (pentafluorophenyl)borate (300 mg, 0.23 mmol) obtained in Example 1 was mixed with dibutyl ether (62 mg, 0.46 mmol) to give the title composition.

$^1$H NMR ($CDCl_3$) δ: 0.87 (6H, t), 0.92 (12H, t), 1.20-1.68 (78H, m), 3.14-3.18 (4H, m), 3.41 (8H, t), 3.62 (2H, q);

$^{19}$F NMR ($CDCl_3$) δ: −66.7 (3F, s), −134.0 (8F, s), −163.3 (4F, t), −167.5 (8H, m).

It was confirmed that the composition obtained in Example 3 was dissolved in n-hexane at 30 wt %.

Example 4

Synthesis of N,N-dioctadecyl-N-(2,2,2-trifluoroethylammonium tetrakis(2-heptafluoronaphthyl)borate A diethyl ether solution (46.9 wt %) (1.0 g, 0.46 mmol) of lithium tetrakis(2-heptafluoronaphthyl)borate produced by a method known per se (e.g., WO 2007/070770) and dioctadecyl-N-(2,2,2-trifluoroethyl)ammonium hydrochloride (0.292 g, 0.46 mmol) were added to dichloromethane (10 mL), and the mixture was stirred at room temperature and partitioned by adding water. The organic layer was dried over anhydrous sodium sulfate and concentrated to give the title compound (0.78 g) as a yellow solid.

$^{1}H$ NMR ($CDCl_3$) δ: 0.87 (6H, t), 1.24 (60H, m), 1.62 (4H, m), 3.20 (4H, t), 3.69 (2H, q);

$^{19}F$ NMR ($CDCl_3$) δ: −63.3 (3F, t), −106.7 (4F, m), −123.4 (4F, m), −143.3 (4F, m), −146.8 (4F, m), −152.5 (4F, m), −155.8 (4F, m), −157.3 (4F, m).

Production Example 4

Synthesis of N-benzyl-N-methyl-2,2,2-trifluoroethylamine

N-Methylbenzylamine (manufactured by KANTO CHEMICAL CO., INC.) (1.1 g, 9.1 mmol) and triethylamine (1.5 g, 15 mmol) were mixed, and 2,2,2-trifluoroethyl trifluoromethanesulfonate (2.2 g, 9.5 mmol) was added at room temperature. The mixture was stirred overnight, 1 M hydrochloric acid was added thereto, and the mixture was extracted with ethyl acetate. The organic layer was washed with water, dried over anhydrous magnesium sulfate, and concentrated under reduced pressure. The residue was purified by column chromatography (n-hexane/ethyl acetate=98/2-90/10) to give the title compound (1.65 g, 86%).

$^{1}H$ NMR ($CDCl_3$) δ: 2.43 (3H, s), 3.03 (2H, q), 3.71 (2H, s), 7.25-7.34 (5H, m); $^{19}F$ NMR ($CDCl_3$) δ: −69.9 (3F, t).

Production Example 5

Synthesis of N-benzyl-N-methyl-2,2,2-trifluoroethylamine hydrochloride

To N-benzyl-N-methyl-2,2,2-trifluoroethylamine (1.65 g, 8.1 mmol) obtained in Production Example 4 was added 1 M hydrogen chloride-diethyl ether solution (20 mL). The mixture was stirred at room temperature for 1 hr, and the solvent was evaporated under reduced pressure to give the title compound (1.97 g, 100%).

$^{1}H$ NMR ($CDCl_3$) δ: 2.96 (3H, s), 3.70-3.81 (2H, m), 4.46 (2H, s), 7.41-7.52 (3H, m), 7.59-7.67 (2H, m);

$^{19}F$ NMR ($CDCl_3$) δ: −63.2 (3F, br s).

Example 5

Synthesis of N-benzyl-N-methyl-2,2,2-trifluoroethylammonium tetrakis(pentafluorophenyl)borate N-Benzyl-N-methyl-2,2,2-trifluoroethylamine hydrochloride (0.30 g, 1.25 mmol) obtained in Production Example 5 was dissolved in chloroform (30 mL), lithium tetrakis(pentafluorophenyl)borate tri-diethyl ether complex (1.10 g, 1.21 mol) was added, and the mixture was stirred at room temperature for 1 hr. Insoluble material was removed by filtration, and the filtrate was concentrated under reduced pressure. The residue was dried under reduced pressure at 45° C. to give the title compound (1.07 g, 93%).

$^{1}H$ NMR ($CDCl_3$) δ: 2.97 (3H, s), 3.60 (2H, q), 4.33 (2H, s), 7.41-7.57 (5H, m);

$^{19}F$ NMR ($CDCl_3$) δ: −65.3 (3F, t), −134.0 (8H, m), −163.4 (4F, t), −167.6 (8F, m).

Production Example 6

Synthesis of N,N-bis(pentafluorophenylmethyl)-1-butylamine

Pentafluorobenzaldehyde (3.0 g, 15.3 mmol), 1-butylamine (0.50 g, 7.0 mmol), and acetic acid (0.40 g) were dissolved in tetrahydrofuran (30 mL), sodium triacetoxyborohydride (3.50 g, 17.0 mmol) was added, and the mixture was stirred at room temperature for 15 hr. The reaction mixture was basified by adding saturated aqueous sodium hydrogen carbonate solution and extracted with diethyl ether. The organic layer was washed with saturated brine, dried over anhydrous sodium sulfate, and concentrated under reduced pressure. The residue was purified by silica gel column chromatography (n-hexane/ethyl acetate=100/0-90/10) to give the title compound (2.65 g, 90%).

$^{1}H$ NMR ($CDCl_3$) δ: 0.81 (3H, t), 1.17-1.23 (2H, m), 1.43-1.48 (2H, m), 2.40 (2H, t), 3.71 (4H, s).

$^{19}F$ NMR ($CDCl_3$) δ: −143.8 (4F, dd), −156.1 (2H, t), −163.4 (4F, m).

Production Example 7

Synthesis of N,N-bis(pentafluorophenylmethyl)-1-butylamine hydrochloride

N,N-Bis(pentafluorophenylmethyl)-1-butylamine (2.30 g, 5.1 mmol) obtained in Production Example 6 was dissolved in n-hexane (30 mL), and 1 M hydrogen chloride-diethyl ether (20 mL) was added. The mixture was stirred at room temperature for 1 hr, and the solvent was evaporated under reduced pressure to give the title compound (1.98 g, 80%).

$^{1}H$ NMR ($CDCl_3$) δ: 0.99 (3H, t), 1.38-1.43 (2H, m), 2.03-2.11 (2H, m), 2.99-3.03 (2H, m), 4.36 (4H, m);

$^{19}F$ NMR ($CDCl_3$) δ: −136.8 (4F, d), −147.9 (2F, t), −159.5 (4H, m).

Example 6

Synthesis of N,N-bis(pentafluorophenylmethyl)-1-butylammonium tetrakis(pentafluorophenyl)borate N,N-Bis(pentafluorophenylmethyl)-1-butylamine hydrochloride (0.93 g, 1.02 mmol) obtained in Production Example 7 was dissolved in chloroform (30 mL), lithium tetrakis(pentafluorophenyl)borate tri-diethyl ether complex (0.50 g, 1.03 mol) was added, and the mixture was stirred at room temperature for 1 hr. Insoluble material was collected by filtration. The insoluble material was dissolved in water and dichloromethane, and the organic layer was separated. The organic layer was dried over anhydrous magnesium sulfate and concentrated under reduced pressure to give the title compound (0.65 g, 65%).

$^{1}H$ NMR (DMSO-$d_6$) δ: 0.77 (3H, t), 1.13-1.22 (2H, m), 1.42-1.48 (2H, m), 2.43-2.50 (2H, m), 4.62 (2H, br s);

$^{19}F$ NMR (DMSO-$d_6$) δ: −132.7 (8F, m), −143.0 (4F, br s), −156.3 (2F, br s), −161.7 (4F, t), −163.3 (4F, br s), −166.2 (8F, m).

Production Example 8

Synthesis of N,N-dioctadecyl-(2,3,4,5,6-pentafluorophenyl)methyl-1-amine

Pentafluorobenzaldehyde (0.50 g, 2.60 mmol) and N,N-dioctadecylamine (1.50 g, 2.87 mmol) were dissolved in tetrahydrofuran (30 mL), sodium triacetoxyborohydride (1.00 g, 4.72 mmol) was added, and the mixture was stirred at room temperature for 15 hr. The reaction mixture was basified by adding saturated aqueous sodium hydrogen carbonate solution and extracted with diethyl ether. The organic layer was washed with saturated brine, dried over anhydrous magnesium sulfate, and concentrated under reduced pressure. The residue was purified by silica gel column chromatography (n-hexane/ethyl acetate=100/0-95/5) to give the title compound (1.05 g, 52%).

$^{1}H$ NMR ($CDCl_3$) δ: 0.88 (6H, t), 1.20-1.30 (64H, m), 2.38 (4H, t), 3.69 (2H, s);

$^{19}F$ NMR ($CDCl_3$) δ: −143.0 (8F, m), −157.1 (4F, m), −163.8 (8F, m).

Production Example 9

Synthesis of N,N-dioctadecyl-(2,3,4,5,6-pentafluorophenyl)methyl-1-amine hydrochloride N,N-Dioctadecyl-(2,3,4,5,6-pentafluorophenyl)methyl-1-amine (2.95 g, 4.2 mmol) obtained in Production Example 8 was dissolved in n-hexane (30 mL), and 1 M hydrogen chloride-diethyl ether (20 mL) was added. The reaction mixture was stirred at room temperature for 1 hr, and the solvent was evaporated under reduced pressure to give the title compound (3.05 g, 98%).

$^{1}H$ NMR ($CDCl_3$) δ: 0.88 (6H, t), 1.21-1.35 (60H, m), 1.88-1.93 (4H, m), 2.92-3.02 (4H, m), 4.32 (2H, s);

$^{19}F$ NMR ($CDCl_3$) δ: −137.4 (1F, d), −148.6 (2F, t), −159.6 (2F, m).

Example 7

Synthesis of N,N-dioctadecyl-(2,3,4,5,6-pentafluorophenyl)methyl-1-ammonium tetrakis(pentafluorophenyl)borate N,N-Dioctadecyl-(2,3,4,5,6-pentafluorophenyl)methyl-1-amine hydrochloride (0.50 g, 0.68 mmol) obtained in Production Example 9 was dissolved in chloroform (30 mL), lithium tetrakis(pentafluorophenyl)borate tri-diethyl ether complex (0.58 g, 0.60 mol) was added, and the mixture was stirred at room temperature for 1 hr. Insoluble material was collected by filtration, and the filtrate was concentrated under reduced pressure at 45° C. to give the title compound (0.83 g, 98%).

$^{1}H$ NMR ($CDCl_3$) δ: 0.88 (6H, t), 1.21-1.30 (60H, m), 1.73 (4H, br s), 3.05 (4H, br s), 4.27 (2H, s);

$^{19}F$ NMR ($CDCl_3$) δ: −134.1 (8H, br s), −139.8 (2H, br s), −146.0 (1H, br s), −158.5 (2H, br s), −163.6 (4H, t), −167.8 (8H, t).

Methylcyclohexane was added to the compound of Example 7 to prepare a 10 wt % methylcyclohexane solution thereof, and the solution was confirmed to be a homogeneous solution.

Production Example 10

Synthesis of N,N-dicyclohexyl-2,2,2-trifluoroacetamide

Dicyclohexylamine (2.0 g, 11 mmol) and triethylamine (1.2 g, 12 mmol) were dissolved in tetrahydrofuran (50 mL), and trifluoroacetic anhydride (2.3 g, 11 mmol) was added dropwise at room temperature. After stirring at room temperature for 1 hr, 1 M hydrochloric acid was added. The mixture was extracted with n-hexane, dried over anhydrous magnesium sulfate, and concentrated under reduced pressure. The residue was purified by silica gel column chromatography (n-hexane/ethyl acetate=100/0-90/10) to give the title compound (2.65 g, 87%).

$^{1}H$ NMR ($CDCl_3$) δ: 1.08-1.84 (14H, m), 2.38-2.48 (4H, m), 3.01-3.08 (2H, m), 3.65-3.68 (2H, m);

$^{19}F$ NMR ($CDCl_3$) δ: −70.3 (3F, s).

Production Example 11

Synthesis of N,N-dicyclohexyl-2,2,2-trifluoroethylamine

N,N-Dicyclohexyl-2,2,2-trifluoroacetamide (2.65 g, 9.56 mmol) obtained in Production Example 10 was dissolved in tetrahydrofuran (30 mL), and 1.0 M borane-tetrahydrofuran complex solution in tetrahydrofuran (20 mL) was added at room temperature. The reaction mixture was stirred at 60° C. for 5 hr, allowed to cool to room temperature, and water (30 mL) was carefully added dropwise under ice-cooling. The mixture was extracted with n-hexane, washed with saturated brine, dried over anhydrous magnesium sulfate, and concentrated under reduced pressure. The residue was purified by silica gel column chromatography (n-hexane/ethyl acetate=100/0-95/5) to give the title compound (2.35 g, 93%).

$^{1}H$ NMR ($CDCl_3$) δ: 0.87-1.25 (10H, m), 1.56-1.78 (10H, m), 2.51-2.57 (2H, m), 3.11 (2H, q);

$^{19}F$ NMR ($CDCl_3$) δ: −72.9 (3F, t).

Production Example 12

Synthesis of N,N-dicyclohexyl-2,2,2-trifluoroethylamine hydrochloride

N,N-Dicyclohexyl-2,2,2-trifluoroethylamine (2.35 g, 8.9 mmol) obtained in Production Example 11 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (2.65 g, 99%).

$^{1}H$ NMR ($CDCl_3$) δ: 1.18-1.40 (6H, m), 1.69-1.81 (6H, m), 1.95-2.07 (4H, m), 2.19 (4H, br s), 3.44-3.52 (2H, m), 3.76 (2H, q);

$^{19}F$ NMR ($CDCl_3$) δ: −59.7 (3F, t).

Example 8

Synthesis of N,N-dicyclohexyl-2,2,2-trifluoroethylammonium tetrakis(pentafluorophenyl)borate N,N-Dicyclohexyl-2,2,2-trifluoroethylamine hydrochloride (0.33 g, 1.1 mmol) obtained in Production Example 12 was dissolved in chloroform (30 mL), lithium tetrakis(pentafluorophenyl)borate tri-diethyl ether complex (1.0 g, 1.1 mmol) was added, and the mixture was stirred at room temperature for 1 hr. Insoluble material was removed by filtration, and the filtrate was concentrated under reduced pressure. The residue was dried under reduced pressure at 45° C. to give the title compound (0.98 g, 94%).

$^1$H NMR ($CDCl_3$) δ: 1.13-2.06 (20H, m), 3.42-3.48 (2H, m), 3.66 (2H, q);

$^{19}$F NMR ($CDCl_3$) δ: −66.0 (3F, s), −134.0 (8H, m), −163.8 (4F, m), −167.8 (8F, m).

Production Example 13

Synthesis of N,N-dihexyl-2,2-difluoroethylamine

1-Hexanal (2.5 g, 25 mmol) and 2,2-difluoroethylamine (1 g, 12 mmol) were dissolved in tetrahydrofuran (30 mL), sodium triacetoxyborohydride (6 g, 28 mmol) was added, and the mixture was stirred at room temperature for 15 hr. The reaction mixture was basified by adding saturated aqueous sodium hydrogen carbonate solution and extracted with diethyl ether. The organic layer was washed with saturated brine, dried over anhydrous sodium sulfate, and concentrated under reduced pressure. The residue was purified by silica gel column chromatography (n-hexane/ethyl acetate-100/0-95/5) to give the title compound (2.98 g, 97%).

$^1$H NMR ($CDCl_3$) δ: 0.87 (6H, t), 1.21-1.44 (16H, m), 2.46-2.50 (4H, m), 2.76 (2H, dt), 5.74 (1H, tt);

$^{19}$F NMR ($CDCl_3$) δ: −120.4 (2F, dt).

Production Example 14

Synthesis of N,N-dihexyl-2,2-difluoroethylamine hydrochloride

N,N-Dihexyl-2,2-difluoroethylamine (2.95 g, 11.8 mmol) obtained in Production Example 13 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (3.05 g, 90%).

$^1$H NMR ($CDCl_3$) δ: 0.90 (6H, t), 1.30-1.41 (12H, m), 1.78-1.86 (4H, m), 3.07-3.17 (4H, m), 3.36-3.45 (2H, m), 6.78 (1H, tt);

$^{19}$F NMR ($CDCl_3$) δ: −118.3 (2H, dt).

Example 9

Synthesis of N,N-dihexyl-2,2-difluoroethylammonium tetrakis(pentafluorophenyl)borate N,N-Dihexyl-2,2-difluoroethylamine hydrochloride (0.40 g, 1.4 mmol) obtained in Production Example 14 was dissolved in chloroform (30 mL), lithium tetrakis(pentafluorophenyl)borate tri-diethyl ether complex (1.25 g, 1.38 mmol) was added, and the mixture was stirred at room temperature for 1 hr. Insoluble material was removed by filtration, and the filtrate was concentrated under reduced pressure. The residue was dried under reduced pressure at 45° C. to give the title compound (1.04 g, 81%).

$^1$H$^-$ NMR ($CDCl_3$) δ: 0.88 (6H, t), 1.24-1.36 (12H, m), 1.64-1.72 (4H, m), 3.16-3.21 (4H, m), 3.40-3.48 (2H, m), 6.18 (1H, t);

$^{19}$F NMR ($CDCl_3$) δ: −65.3 (2F, dt), −134.1 (8H, m), −163.4 (4F, t), −167.6 (8F, m).

Production Example 15

Synthesis of N,N-dihexyl-3,3,3-trifluoropropylamine

1-Hexanal (1 g, 10 mmol), 2,2-difluoroethylamine (0.5 g, 4.0 mmol), and acetic acid (0.3 mL) were dissolved in tetrahydrofuran (30 mL), sodium triacetoxyborohydride (2.5 g, 12 mmol) was added, and the mixture was stirred at room temperature for 15 hr. The mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (1.35 g, 100%).

$^1$H NMR ($CDCl_3$) δ: 0.87-0.92 (6H, m), 1.25-1.45 (16H, m), 2.16-2.29 (2H, m), 2.36-2.41 (4H, m), 2.67-2.71 (2H, m);

$^{19}$F NMR ($CDCl_3$) δ: −66.5 (3F, t).

Production Example 16

Synthesis of N,N-dihexyl-3,3,3-trifluoropropylamine hydrochloride

N,N-Dihexyl-3,3,3-trifluoropropylamine (1.0 g, 3.55 mmol) obtained in Production Example 15 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (1.1 g, 97%).

$^1$H NMR ($CDCl_3$) δ: 0.90 (6H, t), 1.31-1.39 (12H, m), 1.77-1.84 (4H, m), 2.87-2.99 (1H, m), 3.00-3.05 (3H, m), 3.18 (1H, m);

$^{19}$F NMR ($CDCl_3$) δ: −66.6 (3F, t)

Example 10

Synthesis of N,N-dihexyl-3,3,3-trifluoropropylammonium tetrakis(pentafluorophenyl)borate N,N-Dihexyl-3,3,3-trifluoropropylamine hydrochloride (0.30 g, 0.94 mmol) obtained in Production Example 16 was dissolved in chloroform (30 mL), lithium tetrakis(pentafluorophenyl)borate tri-diethyl ether complex (0.85 g, 0.94 mmol) was added, and the mixture was stirred at room temperature for 1 hr. Insoluble material was removed by filtration, and the filtrate was concentrated under reduced pressure. The residue was dried under reduced pressure at 45° C. to give the title compound (0.90 g, 100%).

$^1$H NMR ($CDCl_3$) δ: 0.87 (6H, t), 1.21-1.35 (12H, m), 1.63-1.69 (4H, m), 2.56-2.61 (2H, m), 3.07 (4H, m), 3.30-3.35 (2H, m);

$^{19}$F NMR ($CDCl_3$) δ: −66.4 (3F, t), −134.1 (8F, br s), −163.4 (4F, t), −167.7 (8F, m).

Production Example 17

Synthesis of N,N-dioctadecyl-2,2,3,3,3-pentafluoropropylamine

1-Octadecanal (1.5 g, 5.59 mmol), 2,2,3,3,3-pentafluoropropylamine (0.40 g, 2.7 mmol), and acetic acid (0.3 mL)

were dissolved in tetrahydrofuran (30 mL), sodium triacetoxyborohydride (1.2 g, 5.7 mmol) was added, and the mixture was stirred at room temperature for 15 hr. The mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (1.65 g, 100%).

$^{1}$H NMR ($CDCl_3$) 5:0.88 (6H, t), 1.25-1.43 (64H, m), 2.56 (4H, br s), 2.95-3.10 (2H, m);

$^{19}$F NMR ($CDCl_3$) δ: −85.2 (3F, br s), −121.2 (2F, br s).

Production Example 18

Synthesis of N,N-dioctadecyl-2,2,3,3,3-pentafluoropropylamine hydrochloride

N,N-Dioctadecyl-2,2,3,3,3-pentafluoropropylamine (1.5 g, 2.29 mmol) obtained in Production Example 17 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (1.45 g, 92%).

$^{1}$H NMR ($CDCl_3$) δ: 0.88 (6H, t), 1.19-1.40 (64H, m), 1.94 (4H, br s), 3.22 (4H, t), 3.77 (2H, t);

$^{19}$F NMR ($CDCl_3$) δ: −86.3 (3F, br s), −117.8 (2H, t).

Example 11

Synthesis of N,N-dioctadecyl-2,2,3,3,3-pentafluoropropylammonium tetrakis(pentafluorophenyl)borate N,N-Dioctadecyl-2,2,3,3,3-pentafluoropropylamine hydrochloride (0.50 g, 0.72 mmol) obtained in Production Example 18 was dissolved in chloroform (30 mL), lithium tetrakis(pentafluorophenyl)borate tri-diethyl ether complex (0.65 g, 0.72 mmol) was added, and the mixture was stirred at room temperature for 1 hr. Insoluble material was removed by filtration, and the filtrate was concentrated under reduced pressure. The residue was dried under reduced pressure at 45° C. to give the title compound (0.89 g, 93%).

$^{1}$H NMR ($CDCl_3$) δ: 0.88 (6H, t), 1.18-1.31 (64H, m), 1.72 (4H, br s), 3.21-3.23 (4H, m), 3.67 (2H, t);

$^{19}$F NMR ($CDCl_3$) δ: −85.9 (3F, t), −118.6 (2F, m), −134.0 (8F, br s), −163.4 (4F, t), −167.6 (8F, m).

Methylcyclohexane was added to the compound of Example 11 to prepare a 10 wt % methylcyclohexane solution thereof, and the solution was confirmed to be a homogeneous solution.

Production Example 19

Synthesis of N,N-dioctyl-2,2,2-trifluoroethylamine

1-Octanal (5.5 g, 43 mmol), 2,2,2-trifluoroethylamine (2.0 g, 20 mmol), and acetic acid (0.5 mL) were dissolved in tetrahydrofuran (50 mL), sodium triacetoxyborohydride (10 g, 47 mmol) was added, and the mixture was stirred at room temperature for 15 hr. The reaction mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (5.56 g, 85%).

$^{1}$H NMR ($CDCl_3$) δ: 0.88 (6H, t), 1.27-1.43 (24H, m), 2.56 (4H, t), 3.00 (2H, q);

$^{19}$F NMR ($CDCl_3$) δ: −71.3 (3F, s).

Production Example 20

Synthesis of N,N-dioctyl-2,2,2-trifluoroethylamine hydrochloride

N,N-Dioctyl-2,2,2-trifluoroethylamine (1.5 g, 4, 64 mmol) obtained in Production Example 19 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (1.45 g, 87%).

$^{1}$H NMR ($CDCl_3$) δ: 0.88 (6H, t), 1.26-1.34 (20H, m), 1.94 (4H, br s), 3.15 (4H, br s), 3.78 (2H, q);

$^{19}$F NMR ($CDCl_3$) δ: −63.4 (3F, t).

Example 12

Synthesis of N,N-dioctyl-2,2,2-trifluoroethylammonium tetrakis(pentafluorophenyl)borate N,N-Dioctyl-2,2,2-trifluoroethylamine hydrochloride (0.50 g, 1.39 mmol) obtained in Production Example 20 was dissolved in chloroform (10 mL), lithium tetrakis(pentafluorophenyl)borate tri-diethyl ether complex (1.25 g, 1.38 mmol) was added, and the mixture was stirred at room temperature for 1 hr. Insoluble material was removed by filtration, and the filtrate was concentrated under reduced pressure. The residue was dried under reduced pressure at 45° C. to give the title compound (1.25 g, 87%).

$^{1}$H NMR ($CDCl_3$) δ: 0.86 (6H, t), 1.19-1.29 (20H, m), 1.67-1.73 (4H, m), 3.18-3.22 (4H, m), 3.62-3.67 (2H, m);

$^{19}$F NMR ($CDCl_3$) δ: −66.0 (3F, t), −134.1 (8F, br s), −163.4 (4F, t), −167.6 (8F, m).

Production Example 21

Synthesis of N,N-didodecyl-2,2,2-trifluoroethylamine

1-Dodecanal (5.5 g, 30 mmol), 2,2,2-trifluoroethylamine (1.5 g, 15 mmol), and acetic acid (0.5 mL) were dissolved in tetrahydrofuran (50 mL), sodium triacetoxyborohydride (7 g, 33 mmol) was added, and the mixture was stirred at room temperature for 15 hr. The reaction mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (6.5 g, 99%).

$^{1}H$ NMR ($CDCl_3$) δ: 0.88 (6H, t), 1.26-1.43 (40H, m), 2.56 (4H, t), 3.00 (2H, q);

$^{19}F$ NMR ($CDCl_3$) δ: −71.3 (3F, t).

Production Example 22

Synthesis of N,N-didodecyl-2,2,2-trifluoroethylamine hydrochloride

N,N-Didodecyl-2,2,2-trifluoroethylamine (0.5 g, 1.06 mmol) obtained in Production Example 21 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (2.09 g, 96%).

$^{1}H$ NMR ($CDCl_3$) δ: 0.87 (6H, t), 1.26-1.34 (36H, m), 1.93 (4H, br s), 3.15 (4H, br s), 3.78 (2H, q);

$^{19}F$ NMR ($CDCl_3$) δ: −63.4 (3F, t).

Example 13

Synthesis of N,N-didodecyl-2,2,2-trifluoroethylammonium tetrakis(pentafluorophenyl)borate N,N-Didodecyl-2,2,2-trifluoroethylamine hydrochloride (0.50 g, 1.06 mmol) obtained in Production Example 22 was dissolved in chloroform (30 mL), lithium tetrakis(pentafluorophenyl)borate tri-diethyl ether complex (0.96 g, 1.06 mmol) was added, and the mixture was stirred at room temperature for 1 hr. Insoluble material was removed by filtration, and the filtrate was concentrated under reduced pressure. The residue was dried under reduced pressure at 45° C. to give the title compound (1.19 g, 100%).

$^{1}H$ NMR ($CDCl_3$) δ: 0.87 (6H, t), 1.19-1.29 (36H, m), 1.65-1.71 (4H, m), 3.15-3.22 (4H, m), 3.65 (2H, q);

$^{19}F$ NMR ($CDCl_3$) δ: −66.4 (3F, br s), −134.0 (8F, m), −163.4 (4F, t), −167.6 (8F, m).

Methylcyclohexane was added to the compound of Example 13 to prepare a 10 wt % methylcyclohexane solution thereof, and the solution was confirmed to be a homogeneous solution.

Production Example 23

Synthesis of N,N-dioctadecyl-2,2-difluoroethylamine

1-Octadecanal (3.0 g, 11 mmol), 2,2-difluoroethylamine (0.45 g, 5.6 mmol), and acetic acid (0.3 mL) were dissolved in tetrahydrofuran (30 mL), sodium triacetoxyborohydride (2.50 g, 12 mmol) was added, and the mixture was stirred at room temperature for 15 hr. The reaction mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (2.9 g, 89%).

$^{1}H$ NMR ($CDCl_3$) δ: 0.89 (6H, t), 1.17-1.47 (64H, m), 2.49 (4H, t), 2.77 (2H, dt), 5.75 (1H, t);

$^{19}F$ NMR ($CDCl_3$) δ: −120.4 (2H, dt).

Production Example 24

Synthesis of N,N-dioctadecyl-2,2-difluoroethylamine hydrochloride

N,N-Dioctadecyl-2,2-difluoroethylamine (2.0 g, 3.41 mmol) obtained in Production Example 23 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (2.09 g, 98%).

$^{1}H$ NMR ($CDCl_3$) δ: 0.88 (6H, t), 1.18-1.41 (58H, m), 1.79-1.83 (4H, m), 3.07-3.11 (4H, m), 3.32-3.38 (4H, m), 6.78 (1H, t);

$^{19}F$ NMR ($CDCl_3$) δ: −118.2 (2F, dt).

Example 14

Synthesis of N,N-dioctadecyl-2,2-difluoroethylammonium tetrakis(pentafluorophenyl)borate N,N-Dioctadecyl-2,2-difluoroethylamine hydrochloride (0.50 g, 0.80 mmol) obtained in Production Example 24 was dissolved in chloroform (30 mL), lithium tetrakis(pentafluorophenyl)borate tri-diethyl ether complex (0.72 g, 0.79 mmol) was added, and the mixture was stirred at room temperature for 1 hr. Insoluble material was removed by filtration, and the filtrate was concentrated under reduced pressure. The residue was dried under reduced pressure at 45° C. to give the title compound (0.97 g, 97%).

$^{1}H$ NMR ($CDCl_3$) δ: 0.86 (3H, t), 1.17-1.43 (58H, m), 1.71 (4H, br s), 3.16 (4H, br s), 3.42 (2H, t), 6.25 (1H, t);

$^{19}F$ NMR ($CDCl_3$) δ: −121.3 (2F, d), −134.0 (8F, d), −163.4 (8F, t), −167.6 (8F, t).

Methylcyclohexane was added to the compound of Example 14 to prepare a 10 wt % methylcyclohexane solution thereof, and the solution was confirmed to be a homogeneous solution.

Production Example 25

Synthesis of 1-(2,2,2-trifluoroethyl)piperidine hydrochloride 1-(2,2,2-Trifluoroethyl)piperidine (1.5 g, 8.97 mmol) was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (1.85 g, 100%).

$^{1}H$ NMR ($CDCl_3$) δ: 1.43-1.94 (4H, m), 2.37 (2H, br s), 3.10 (2H, br s), 3.56 (2H, br s), 3.77 (2H, t);

$^{19}F$ NMR ($CDCl_3$) δ: −63.0 (3F, t).

Example 15

Synthesis of 1-(2,2,2-trifluoroethyl)piperidinium tetrakis(pentafluorophenyl)borate 1-(2,2,2-Trifluoroethyl)piperidine hydrochloride (0.30 g, 1.47 mmol) obtained in Production Example 25 was dissolved in chloroform (30 mL), lithium tetrakis(pentafluorophenyl)borate tri-diethyl ether complex (1.33 g, 1.46 mmol) was added, and the mixture was stirred at room temperature for 1 hr. Insoluble material was removed by filtration, and the filtrate was concentrated under reduced pressure. The residue was dried under reduced pressure at 45° C. to give the title compound (1.19 g, 96%).

$^1$H NMR ($CDCl_3$) δ: 1.47-1.62 (2H, m), 1.92-1.99 (2H, m), 2.10-2.20 (2H, m), 3.01 (2H, br s), 3.57-3.63 (4H, m);

$^{19}$F NMR ($CDCl_3$) δ: −63.2 (3F, t), −134.0 (8F, br s), −163.8 (4F, t), −167.9 (8F, m).

Production Example 26

Synthesis of N,N-dioctadecyl-3,3,3-trifluoropropylamine

1-Octadecanal (2.4 g, 8.94 mmol), 3,3,3-trifluoropropylamine (0.50 g, 4.42 mmol), and acetic acid (0.3 mL) were dissolved in tetrahydrofuran (30 mL), sodium triacetoxyborohydride (2.10 g, 9.9 mmol) was added, and the mixture was stirred at room temperature for 15 hr. The reaction mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (2.4 g, 88%).

$^1$H NMR ($CDCl_3$) δ: 0.88 (6H, t), 1.18-1.43 (64H, m), 2.23-2.27 (2H, m), 2.38-2.44 (4H, m), 2.70 (2H, t);

$^{19}$F NMR ($CDCl_3$) δ: −66.5 (3F, t).

Production Example 27

Synthesis of N,N-dioctadecyl-3,3,3-trifluoropropylamine hydrochloride

N,N-Dioctadecyl-3,3,3-trifluoropropylamine (1.5 g, 2.43 mmol) obtained in Production Example 26 was dissolved in n-hexane (10 mL), 1.0 M hydrogen chloride-diethyl ether solution (10 mL) was added, and the mixture was stirred for 3 hr. The precipitate was collected by filtration, washed with n-hexane, and dried under reduced pressure to give the title compound (1.45 g, 91%).

$^1$H NMR ($CDCl_3$) δ: 0.88 (6H, t), 1.19-1.40 (60H, m), 1.70-1.81 (4H, m), 2.86-3.03 (6H, m), 3.17-3.22 (2H, m);

$^{19}$F NMR ($CDCl_3$) δ: −66.6 (3F, t).

Example 16

Synthesis of N,N-dioctadecyl-3,3,3-trifluoropropylammonium tetrakis(pentafluorophenyl)borate N,N-Dioctadecyl-3,3,3-trifluoropropylamine hydrochloride (0.50 g, 0.764 mmol) obtained in Production Example 27 was dissolved in chloroform (30 mL), lithium tetrakis (pentafluorophenyl)borate tri-diethyl ether complex (0.65 g, 0.72 mmol) was added, and the mixture was stirred at room temperature for 1 hr. Insoluble material was removed by filtration, and the filtrate was concentrated under reduced pressure. The residue was dried under reduced pressure at 70° C. to give the title compound (0.89 g, 96%).

$^1$H NMR ($CDCl_3$) δ: 0.88 (6H, t), 1.18-1.38 (60H, m), 1.65-1.72 (4H, m), 2.60-2.67 (2H, m), 3.04-3.07 (4H, m), 3.27-3.32 (2H, m);

$^{19}$F NMR ($CDCl_3$) δ: −64.4 (3F, t), −131.8 (8F, m), −161.4 (4F, m), −165.6 (8F, m).

Methylcyclohexane was added to the compound of Example 16 to prepare a 10 wt % methylcyclohexane solution thereof, and the solution was confirmed to be a homogeneous solution.

Production Example 28

Synthesis of N,N-dioctadecyl-2-fluoroethylamine

1-Octadecanal (3.0 g, 11 mmol) and a tert-butanol solution (10 wt %, 3.3 g, 5.2 mmol) of 2-fluoroethylamine, and acetic acid (0.3 mL) were dissolved in tetrahydrofuran (30 mL), sodium triacetoxyborohydride (2.50 g, 12 mmol) was added, and the mixture was stirred at room temperature for 15 hr. The reaction mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-90/10) to give the title compound (2.02 g, 32%).

$^1$H NMR ($CDCl_3$) δ: 0.88 (6H, t), 1.18-1.64 (65H, m), 2.44-2.51 (4H, m), 2.77 (2H, dt), 4.50 (1H, dt);

$^{19}$F NMR ($CDCl_3$) δ: −2220.6 (1F, br s).

Production Example 29

Synthesis of N,N-dioctadecyl-2-fluoroethylamine hydrochloride

N,N-Dioctadecyl-2-fluoroethylamine (1.50 g, 2.64 mmol) obtained in Production Example 28 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (1.45 g, 91%).

$^1$H NMR ($CDCl_3$) δ: 0.88 (6H, t), 1.19-1.40 (60H, m), 1.78-1.82 (4H, m), 3.04-3.11 (4H, m), 3.32-3.40 (2H, m), 5.02 (2H, dt);

$^{19}$F NMR ($CDCl_3$) δ: −223.5 (1F, m).

Example 17

Synthesis of N,N-dioctadecyl-2-fluoroethylammonium tetrakis(pentafluorophenyl)borate N,N-Dioctadecyl-2-fluoroethylamine hydrochloride (0.50 g, 0.83 mmol) obtained in Production Example 29 was dissolved in chloroform (30 mL), lithium tetrakis(pentafluorophenyl)borate tri-diethyl ether complex (0.75 g, 0.83 mmol) was added, and the mixture was stirred at room temperature for 1 hr. Insoluble material was removed by filtration, and the filtrate was concentrated under reduced pressure. The residue was dried under reduced pressure at 70° C. to give the title compound (0.89 g, 86%).

$^1$H NMR ($CDCl_3$) δ: 0.88 (6H, t), 1.18-1.31 (60H, m), 1.65-1.73 (4H, m), 3.11-3.13 (4H, m), 3.34-3.43 (2H, m), 4.76 (2H, dt);

$^{19}$F NMR ($CDCl_3$) δ: −133.9 (8F, br s), −163.3 (4F, t), −167.5 (8F, m), −223.4 (1H, br s).

Methylcyclohexane was added to the compound of Example 17 to prepare a 10 wt % methylcyclohexane solution thereof, and the solution was confirmed to be a homogeneous solution.

Production Example 30

Synthesis of 1,4-bis(2,2,2-trifluoroethyl)piperazine

To 1,4-bis(trifluoroacetyl)piperazine (3.5 g, 13 mmol) in tetrahydrofuran (30 mL) was added a tetrahydrofuran solution (40 mL, 40 mmol) of 1 M borane-tetrahydrofuran complex at room temperature, and the mixture was stirred at 60° C. for 3 hr. The mixture was ice-cooled, water was carefully added, and the mixture was extracted with n-hexane. The organic layer was washed with saturated brine, dried over anhydrous sodium sulfate, and concentrated under reduced pressure. The residue was purified by silica gel column chromatography (n-hexane/ethyl acetate=95/5-80/20) to give the title compound (2.08 g, 66%).

$^1$H NMR ($CDCl_3$) δ: 2.71 (8H, s), 2.96 (4H, q);

$^{19}$F NMR ($CDCl_3$) δ: −70.2 (6F, t).

Production Example 31

Synthesis of 1,4-bis(2,2,2-trifluoroethyl)piperazine dihydrochloride 1,4-Bis(2,2,2-trifluoroethyl)piperazine (1.50 g, 6.0 mmol) obtained in Production Example 30 was dissolved in n-hexane (30 mL), 1.0 M hydrogen chloride-diethyl ether solution (20 mL) was added, and the mixture was stirred for 1 hr. The mixture was concentrated under reduced pressure to give the title compound (1.85 g, 96%).

$^1$H NMR (DMSO-$d_6$) δ: 3.03 (8H, br s), 3.67 (4H, br s);

$^{19}$F NMR (DMSO-$d_6$) δ: −65.8 (6F, br s).

Example 18

Synthesis of 1,4-bis(2,2,2-trifluoroethyl)piperazinium bis[tetrakis(pentafluorophenyl)borate]

1,4-Bis(2,2,2-trifluoroethyl)piperazine dihydrochloride (0.50 g, 1.55 mmol) obtained in Production Example 31 was dissolved in dichloromethane (50 mL), lithium tetrakis (pentafluorophenyl)borate tri-diethyl ether complex (2.81 g, 3.09 mmol) was added, and the mixture was stirred at room temperature for 3 hr. Insoluble material was collected by filtration, dissolved in water and dichloromethane, and the organic layer was separated. The organic layer was dried over anhydrous magnesium sulfate, and concentrated under reduced pressure to give the title compound (0.87 g, 35%).

$^1$H NMR (DMSO-$d_6$) δ: 2.78 (8H, br s), 3.93 (4H, br s);

$^{19}$F NMR (DMSO-$d_6$) δ: −67.6 (6F, br s), −132.7 (16F, br s), 161.6 (8F, t), −166.2 (16F, t).

Production Example 32

Synthesis of N,N-didocosyl-2,2,2-trifluoroethylamine

1-Docosanal (4.0 g, 12.3 mmol), 2,2,2-trifluoroethylamine (0.50 g, 5.0 mmol), and acetic acid (0.05 mL) were dissolved in tetrahydrofuran (50 mL), sodium triacetoxyborohydride (2.80 g, 13 mmol) was added, and the mixture was stirred at room temperature for 15 hr. The reaction mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (1.38 g, 40%).

$^1$H NMR ($CDCl_3$) δ: 0.88 (6H, t), 1.25-1.30 (76H, m), 1.40-1.43 (4H, m), 2.56 (4H, t), 3.00 (2H, q);

$^{19}$F NMR ($CDCl_3$) δ: −71.3 (3F, t).

Production Example 33

Synthesis of N,N-didocosyl-2,2,2-trifluoroethylamine hydrochloride

N,N-Didocosyl-2,2,2-trifluoroethylamine (1.30 g, 1.82 mmol) obtained in Production Example 32 was dissolved in n-hexane (30 mL), 1.0 M hydrogen chloride-diethyl ether solution (10 mL) was added, and the mixture was stirred for 1 hr. The reaction mixture was concentrated under reduced pressure to give the title compound (1.34 g, 98%).

$^1$H NMR ($CDCl_3$) δ: 0.88 (6H, t), 1.25-1.40 (76H, m), 1.85-2.00 (4H, m), 3.14 (4H, t), 3.75 (2H, q);

$^{19}$F NMR ($CDCl_3$) δ: −63.5 (3F, t).

Example 19

Synthesis of N,N-didocosyl-2,2,2-trifluoroethylammonium tetrakis(pentafluorophenyl)borate N,N-Didocosyl-2,2,2-trifluoroethylamine hydrochloride (0.40 g, 0.53 mmol) obtained in Production Example 33, lithium tetrakis(pentafluorophenyl)borate mono-diethyl ether complex (0.41 g, 0.53 mmol), and methylcyclohexane (20 mL) were mixed, and the mixture was stirred at room temperature for 3 hr. The reaction mixture was washed with water, and the organic layer was dried over anhydrous magnesium sulfate and concentrated under reduced pressure at 45° C. to give the title compound (0.65 g, 88%).

$^1$H NMR ($CDCl_3$) δ: 0.87 (6H, t), 1.25-1.29 (76H, m), 1.60-1.65 (4H, m), 3.12-3.16 (4H, m). 3.60 (2H, q);

$^{19}$F NMR ($CDCl_3$) δ: −65.9 (3F, t), −132.8 (8F, t), −162.3 (4F, m), −166.2 (8F, m).

Methylcyclohexane was added to the compound of Example 19 to prepare a 10 wt % methylcyclohexane solution thereof, and the solution was confirmed to be a homogeneous solution.

Production Example 34

Synthesis of N,N-(3,7,11,15-tetramethylhexadecyl)-2,2,2-trifluoroethylamine 3,7,11,15-Tetramethylhexadecanal (2.3 g, 7.8 mmol), 2,2,2-trifluoroethylamine (0.20 g, 2.0 mmol), and acetic acid (0.3 mL) were dissolved in tetrahydrofuran (30 mL), sodium triacetoxyborohydride (1.5 g, 7.8 mmol) was added, and the mixture was stirred at room temperature for 15 hr. The reaction mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (1.13 g, 85%).

$^1H$ NMR ($CDCl_3$) δ: 0.84-0.88 (30H, m), 1.07-1.56 (48H, m), 2.57-2.61 (4H, m), 3.00 (2H, q);

$^{19}F$ NMR ($CDCl_3$) δ: −70.9 (3F, t).

Production Example 35

Synthesis of N,N-(3,7,11,15-tetramethylhexadecyl)-2,2,2-trifluoroethylamine hydrochloride N,N-(3,7,11,15-Tetramethylhexadecyl)-2,2,2-trifluoroethylamine (2.35 g, 3.56 mmol) obtained in Production Example 34 was dissolved in n-hexane (20 mL), 1.0 M hydrogen chloride-diethyl ether solution (10 mL) was added, and the mixture was stirred for 1 hr. The reaction mixture was concentrated under reduced pressure to give the title compound (2.48 g, 100%).

$^1$NMR ($CDCl_3$) δ: 0.84-0.95 (30H, m), 1.13-1.57 (48H, m), 3.13-3.25 (4H, m), 3.76 (2H, q);

$^{19}F$ NMR ($CDCl_3$) δ: −63.4 (3F, t).

Example 20

Synthesis of N,N-(3,7,11,15-tetramethylhexadecyl)-2,2,2-trifluoroethylammonium tetrakis(pentafluorophenyl)borate N,N-(3,7,11,15-Tetramethylhexadecyl)-2,2,2-trifluoroethylamine hydrochloride (0.50 g, 0.72 mmol) obtained in Production Example 35, lithium tetrakis(pentafluorophenyl) borate tri-diethyl ether complex (0.66 g, 0.72 mmol), and methylcyclohexane (15 mL) were mixed, and the mixture was stirred at room temperature for 3 hr. The mixture was washed with water, and the organic layer was dried over anhydrous magnesium sulfate and concentrated under reduced pressure at 45° C. to give the title compound (0.96 g, 68%).

$^1H$ NMR ($CDCl_3$) δ: 0.82-0.89 (30H, m), 1.13-1.57 (48H, m), 3.15-3.25 (4H, m), 3.60 (2H, q);

$^{19}F$ NMR ($CDCl_3$) δ: −67.1 (3F, t), −133.9 (8F, d), −164.4 (4F, t) −167.5 (8F, t).

Methylcyclohexane was added to the compound of Example 20 to prepare a 10 wt % methylcyclohexane solution thereof, and the solution was confirmed to be a homogeneous solution.

Production Example 36

Synthesis of N,N-(3,7,11-trimethyldodecyl)-2,2,2-trifluoroethylamine 3,7,11-Trimethyldodecanal (1.2 g, 5.3 mmol), 2,2,2-trifluoroethylamine (0.20 g, 2.0 mmol), and acetic acid (0.3 mL) were dissolved in tetrahydrofuran (30 mL), sodium triacetoxyborohydride (1.5 g, 7.8 mmol) was added, and the mixture was stirred at room temperature for 15 hr. The reaction mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (0.95 g, 91%).

$^1H$ NMR ($CDCl_3$) δ: 0.83-0.88 (24H, m), 1.00-1.57 (34H, m), 2.58-2.60 (4H, m), 3.00 (2H, q);

$^{19}F$ NMR ($CDCl_3$) δ: −71.1 (3F, t).

Example 21

Synthesis of N,N-(3,7,11-trimethyldodecyl)-2,2,2-trifluoroethylammonium tetrakis(pentafluorophenyl)borate N,N-(3,7,11-Trimethyldodecyl)-2,2,2-trifluoroethylamine (0.56 g, 1 mmol) obtained in Production Example 36 was dissolved in methylcyclohexane (20 mL), 1.0 M hydrogen chloride-diethyl ether solution (1 mL) was added, and lithium tetrakis(pentafluorophenyl)borate tri-diethyl ether complex (0.91 g, 1 mmol) was added. The reaction mixture was stirred at room temperature for 1 hr. The mixture was washed with water, and the organic layer was dried over anhydrous magnesium sulfate and concentrated under reduced pressure at 45° C. to give the title compound (1.20 g, 74%).

$^1H$ NMR ($CDCl_3$) δ: 0.81-0.89 (24H, m), 1.03-1.51 (34H, m), 2.95-3.00 (4H, m), 3.41 (2H, q);

$^{19}F$ NMR ($CDCl_3$) δ: −68.2 (3F, t), −133.9 (8F, d), −164.4 (4F, t), −167.5 (8F, t).

Methylcyclohexane was added to the compound of Example 21 to prepare a 10 wt % methylcyclohexane solution thereof, and the solution was confirmed to be a homogeneous solution.

Example 22

Production of composition containing N,N-dioctadecyl-2,2,2-trifluoroethylammonium tetrakis(pentafluorophenyl)borate and N,N-dioctadecyl-2,2,2-trifluoroethylamine N,N-Dioctadecyl-2,2,2-trifluoroethylamine (0.90 g, 1.49 mmol) obtained in Production Example 2 was dissolved in chloroform (30 mL), lithium tetrakis(pentafluorophenyl) borate tri-diethyl ether complex (0.91 g, 1.00 mmol) and 1.0 M hydrogen chloride-diethyl ether solution were added, and the mixture was stirred at room temperature for 1 hr. Insoluble material was removed by filtration, and the filtrate was concentrated under reduced pressure. The residue was dried under reduced pressure at 70° C. to give the title composition (1.51 g).

$^1H$ NMR ($CDCl_3$) δ: 0.86 (6H, t), 1.23-1.30 (60H, m), 1.68-1.76 (4H, m), 3.12-3.16 (4H, m), 3.61 (2H, q);

$^{19}F$ NMR ($CDCl_3$) δ: −65.3 (4.8F, t), −133.9 (8F, m), −163.8 (4F, t), −167.8 (8F, t).

n-Hexane was added to the composition of Example 22 to prepare a 20 wt % n-hexane solution thereof, and the solution was confirmed to be a homogeneous solution.

Isohexane was added to the composition of Example 22 to prepare a 20 wt % isohexane solution thereof, and the solution was confirmed to be a homogeneous solution.

n-Heptane was added to the composition of Example 22 to prepare a 20 wt % n-heptane solution thereof, and the solution was confirmed to be a homogeneous solution.

ISOPAR E (registered trade mark) was added to the composition of Example 22 to prepare a 20 wt % ISOPAR E (registered trade mark) solution thereof, and the solution was confirmed to be a homogeneous solution.

Cyclohexane was added to the composition of Example 22 to prepare a 20 wt % cyclohexane solution thereof, and the solution was confirmed to be a homogeneous solution.

Methylcyclohexane was added to the composition of Example 22 to prepare a 20 wt % methylcyclohexane solution thereof, and the solution was confirmed to be a homogeneous solution.

Production Example 37

Synthesis of N,N-ditetradecyl-2,2,2-trifluoroethylamine

1-Tetradecanal (4.0 g, 18.8 mmol), 2,2,2-trifluoroethylamine (0.90 g, 9.1 mmol), and acetic acid (0.3 mL) were dissolved in tetrahydrofuran (30 mL), sodium triacetoxyborohydride (4.0 g, 18.9 mmol) was added, and the mixture was stirred at room temperature for 15 hr. The reaction mixture was basified by adding saturated aqueous sodium hydrogen carbonate solution and extracted with n-hexane. The organic layer was washed with saturated brine, dried over anhydrous sodium sulfate, and concentrated under reduced pressure. The residue was purified by silica gel column chromatography (n-hexane/ethyl acetate-100/0-95/5) to give the title compound (4.0 g, 89%).

$^1$H NMR ($CDCl_3$) δ: 0.88 (6H, t), 1.26-1.43 (48H, m), 2.55 (4H, t), 3.00 (2H, q);

$^{19}$F NMR ($CDCl_3$) δ: −71.3 (3F, t).

Production Example 38

Synthesis of N,N-ditetradecyl-2,2,2-trifluoroethylamine hydrochloride

N,N-Ditetradecyl-2,2,2-trifluoroethylamine (1.50 g, 3.05 mmol) obtained in Production Example 37 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (1.45 g, 90%).

$^1$H NMR ($CDCl_3$) δ: 0.88 (6H, t), 1.20-1.40 (44H, m), 1.96 (4H, br s), 3.15 (4H, br s), 3.78 (2H, q);

$^{19}$F NMR ($CDCl_3$) δ: −63.4 (3F, t).

Example 23

Synthesis of N,N-ditetradecyl-2,2,2-trifluoroethylammonium tetrakis(pentafluorophenyl)borate N,N-Ditetradecyl-2,2,2-trifluoroethylamine (0.60 g, 1.14 mmol) obtained in Production Example 38 was dissolved in chloroform (30 mL), lithium tetrakis(pentafluorophenyl) borate tri-diethyl ether complex (1.04 g, 1.14 mmol) was added, and the mixture was stirred at room temperature for 1 hr. Insoluble material was removed by filtration, and the filtrate was concentrated under reduced pressure. The residue was dried under reduced pressure at 70° C. to give the title compound (1.34 g, 100%).

$^1$H NMR ($CDCl_3$) δ: 0.88 (6H, t), 1.19-1.36 (44H, m), 1.65-1.70 (4H, m), 3.14-3.18 (4H, m), 3.62 (2H, q);

$^{19}$F NMR ($CDCl_3$) δ: −66.4 (3F, t), −134.0 (8F, m), −163.4 (4F, t), −167.6 (8F, t).

Cyclohexane was added to Example 23 to prepare a 20 wt % cyclohexane solution thereof, and the solution was confirmed to be a homogeneous solution.

Example 24

Production of composition containing N,N-ditetradecyl-2,2,2-trifluoroethylammonium tetrakis(pentafluorophenyl)borate and didodecyl ether N,N-Ditetradecyl-2,2,2-trifluoroethylammonium tetrakis (pentafluorophenyl)borate (58 mg, 0.05 mmol) obtained in Example 23 and didodecyl ether (40 mg, 0.10 mmol) were added and mixed to give the title composition.

$^1$H NMR ($CDCl_3$) δ: 0.85-0.88 (18H, m), 1.24-1.35 (116H, m), 1.51-1.58 (8H, m), 1.64-1.70 (4H, m), 3.11-3.15 (4H, m), 3.38 (8H, t), 3.60 (2H, q);

$^{19}$F NMR ($CDCl_3$) δ: −66.6 (3F, s), −134.0 (8F, s), −163.5 (4F, t), −167.6 (8F, t).

n-Hexane was added to the composition of Example 24 to prepare a 20 wt % n-hexane solution thereof, and the solution was confirmed to be a homogeneous solution.

Production Example 39

Synthesis of N,N-dihexadecyl-2,2,2-trifluoroethylamine

1-Hexadecanal (4.0 g, 16.6 mmol), 2,2,2-trifluoroethylamine (0.84 g, 8.5 mmol), and acetic acid (0.5 mL) were dissolved in tetrahydrofuran (50 mL), sodium triacetoxyborohydride (4.0 g, 18.9 mmol) was added, and the mixture was stirred at room temperature for 15 hr. The reaction mixture was basified by adding saturated aqueous sodium hydrogen carbonate solution, and extracted with n-hexane. The organic layer was washed with saturated brine, dried over anhydrous sodium sulfate, and concentrated under reduced pressure. The residue was purified by silica gel column chromatography (n-hexane/ethyl acetate=100/0-95/5) to give the title compound (4.56 g, 98%).

$^1$H NMR ($CDCl_3$) δ: 0.88 (6H, t), 1.26-1.43 (56H, m), 2.56 (4H, t), 3.00 (2H, q);

$^{19}$F NMR ($CDCl_3$) δ: −71.3 (3F, t).

Production Example 40

Synthesis of N,N-dihexadecyl-2,2,2-trifluoroethylamine hydrochloride

N,N-Dihexadecyl-2,2,2-trifluoroethylamine (1.50 g, 2.74 mmol) obtained in Production Example 39 was dissolved in n-hexane (30 mL), 1.0 M hydrogen chloride-diethyl ether solution (20 mL) was added, and the mixture was stirred for 1 hr. The reaction mixture was concentrated under reduced pressure to give the title compound (1.55 g, 97%).

$^1$H NMR ($CDCl_3$) δ: 0.88 (6H, t), 1.19-1.40 (52H, m), 1.93 (4H, br s), 3.15 (4H, br s), 3.77 (2H, q);

$^{19}$F NMR ($CDCl_3$) δ: −63.4 (3F, t).

Example 25

Synthesis of N,N-dihexadecyl-2,2,2-trifluoroethylammonium tetrakis(pentafluorophenyl)borate N,N-Dihexadecyl-2,2,2-trifluoroethylamine (0.60 g, 1.03 mmol) obtained in Production Example 40 was dissolved in chloroform (30 mL), lithium tetrakis(pentafluorophenyl) borate tri-diethyl ether complex (0.95 g, 1.05 mmol) was added, and the mixture was stirred at room temperature for 1 hr. Insoluble material was removed by filtration, and the filtrate was concentrated under reduced pressure. The residue was dried under reduced pressure at 70° C. to give the title compound (1.51 g).

$^1$H NMR ($CDCl_3$) δ: 0.88 (6H, t), 1.19-1.36 (54H, m), 1.65-1.70 (4H, m), 3.14-3.18 (4H, m), 3.62 (2H, q);

$^{19}$F NMR ($CDCl_3$) δ: −66.4 (3F, t), −134.0 (8F, m), −163.4 (4F, t), −167.6 (8F, t).

Cyclohexane was added to the composition obtained in Example 25 to prepare a 20 wt % cyclohexane solution thereof, and the solution was confirmed to be a homogeneous solution.

Example 26

Production of composition containing N,N-dihexadecyl-2,2,2-trifluoroethylammonium tetrakis(pentafluorophenyl) borate and dihexadecyl ether N,N-Dihexadecyl-2,2,2-trifluoroethylammonium tetrakis (pentafluorophenyl)borate (60 mg, 0.05 mmol) obtained in Example 25 and dihexadecyl ether (23 mg, 0.05 mmol) were added and mixed to give the title composition.

$^1$H NMR ($CDCl_3$) δ: 0.86-0.90 (12H, m), 1.20-1.36 (104H, m), 1.52-1.58 (4H, m), 1.63-1.70 (4H, m), 3.15-3.19 (4H, m), 3.39 (4H, t), 3.64 (2H, q);

$^{19}$F NMR ($CDCl_3$) δ: −66.7 (3F, s), −134.1 (8F, s), −163.5 (4F, t), −167.6 (8F, t).

n-Hexane was added to the composition of Example 26 to prepare a 20 wt % n-hexane solution thereof, and the solution was confirmed to be a homogeneous solution.

Example 27

Production of composition containing N,N-dioctadecyl-2,2,2-trifluoroethylammonium tetrakis(pentafluorophenyl)borate and dioctyl ether N,N-Dioctadecyl-2,2,2-trifluoroethylammonium tetrakis (pentafluorophenyl)borate (64 mg, 0.05 mmol) obtained in Example 1 and dioctyl ether (12 mg, 0.05 mmol) were added and mixed to give the title composition.

$^1$H NMR ($CDCl_3$) δ: 0.88 (12H, t), 1.20-1.37 (80H, m), 1.52-1.58 (4H, m), 1.65-1.70 (4H, m), 3.14-3.19 (4H, m), 3.39 (4H, t), 3.63 (2H, q);

$^{19}$F NMR ($CDCl_3$) δ: −66.6 (3F, br s), −134.0 (8F, br s), −163.4 (4F, t), −167.6 (8F, t).

n-Hexane was added to the composition of Example 27 to prepare a 20 wt % n-hexane solution thereof, and the solution was confirmed to be a homogeneous solution.

Example 28

Production of composition containing N,N-dioctadecyl-2,2,2-trifluoroethylammonium tetrakis(pentafluorophenyl)borate and didodecyl ether N,N-Dioctadecyl-2,2,2-trifluoroethylammonium tetrakis (pentafluorophenyl)borate (64 mg, 0.05 mmol) obtained in Example 1 and didodecyl ether (15 mg, 0.05 mmol) were added and mixed to give the title composition.

$^1$H NMR ($CDCl_3$) δ: 0.86-0.90 (12H, m), 1.20-1.38 (96H, m), 1.53-1.60 (4H, m), 1.65-1.72 (4H, m), 3.15-3.20 (4H, m), 3.39 (4H, t), 3.65 (2H, q);

$^{19}$F NMR ($CDCl_3$) δ: −66.4 (3F, br s), −134.0 (8F, br s), −163.4 (4F, t), −167.5 (8F, m).

n-Hexane was added to the composition of Example 28 to prepare a 20 wt % n-hexane solution thereof, and the solution was confirmed to be a homogeneous solution.

Example 29

Production of composition containing N,N-dioctadecyl-2,2,2-trifluoroethylammonium tetrakis(pentafluorophenyl)borate and dihexadecyl ether N,N-Dioctadecyl-2,2,2-trifluoroethylammonium tetrakis (pentafluorophenyl)borate (64 mg, 0.05 mmol) obtained in Example 1 and dihexadecyl ether (23 mg, 0.05 mmol) were added and mixed to give the title composition.

$^1$H NMR ($CDCl_3$) δ: 0.86-0.98, (12H, m), 1.20-1.35 (112H, m), 1.52-1.75 (8H, m), 3.15-3.20 (4H, m), 3.39 (4H, t), 3.65 (2H, q);

$^{19}$F NMR ($CDCl_3$) δ: −66.5 (3F, br s), −134.2 (8F, br s), −163.6 (4F, t), −167.7 (8F, m).

n-Hexane was added to the composition of Example 29 to prepare a 20 wt % n-hexane solution thereof, and the solution was confirmed to be a homogeneous solution.

Example 30

Production of composition containing N,N-dioctadecyl-2,2,2-trifluoroethylammonium tetrakis(pentafluorophenyl)borate and diphenyl ether N,N-Dioctadecyl-2,2,2-trifluoroethylammonium tetrakis (pentafluorophenyl)borate (64 mg, 0.05 mmol) obtained in Example 1 and diphenyl ether (8.5 mg, 0.05 mmol) were added and mixed to give the title composition.

$^1$H NMR ($CDCl_3$) δ: 0.86-0.90, (6H, m), 1.20-1.40 (58H, m), 1.62-1.68 (4H, m), 3.12-3.16 (4H, m), 3.61 (4H, q), 6.99-7.03 (4H, m), 7.08-7.12 (2H, m), 7.31-7.36 (4H, m);

$^{19}$F NMR ($CDCl_3$) δ: −66.9 (3F, br s), −134.1 (8F, br s), −163.4 (4F, t), −167.6 (8F, m).

n-Hexane was added to the composition of Example 30 to prepare a 20 wt % n-hexane solution thereof, and the solution was confirmed to be a homogeneous solution.

Example 31

Production of composition containing N,N-dioctadecyl-2,2,2-trifluoroethylammonium tetrakis(pentafluorophenyl)borate and octadecyl phenyl ether N,N-Dioctadecyl-2,2,2-trifluoroethylammonium tetrakis (pentafluorophenyl)borate (64 mg, 0.05 mmol) obtained in Example 1 and octadecyl phenyl ether (18 mg, 0.05 mmol) were added and mixed to give the title composition.

$^1$H NMR ($CDCl_3$) δ: 0.84-0.98 (12H, m), 1.20-1.44 (85H, m), 1.62-1.81 (6H, m), 3.13-3.18 (4H, m), 3.61 (4H, q), 3.95 (2H, t), 6.88-6.94 (2H, m), 7.25-7.30 (3H, m);

$^{19}$F NMR ($CDCl_3$) δ: −66.8 (3F, br s), −134.1 (8F, br s), −163.4 (4F, t), −167.6 (8F, m).

n-Hexane was added to the composition of Example 31 to prepare a 20 wt % n-hexane solution thereof, and the solution was confirmed to be a homogeneous solution.

Example 32

Production of composition containing N,N-dioctadecyl-2,2,2-trifluoroethylammonium tetrakis(pentafluorophenyl)borate and cyclopentyl methyl ether N,N-Dioctadecyl-2,2,2-trifluoroethylammonium tetrakis (pentafluorophenyl)borate (64 mg, 0.05 mmol) obtained in Example 1 and cyclopentyl methyl ether (10 mg, 0.10 mmol) were added and mixed to give the title composition.

$^1$H NMR ($CDCl_3$) δ: 0.88 (6H, t), 1.20-1.35 (60H, m), 1.53-1.56 (4H, m), 1.61-1.76 (16H, m), 3.12-3.17 (4H, m), 3.28 (6H,$), 3.61 (2H, q), 3.79-3.83 (2H, m);

$^{19}$F NMR ($CDCl_3$) δ: −66.6 (3F, br s), −133.9 (8F, br s), −163.5 (4F, t), −167.6 (8F, m).

n-Hexane was added to the composition of Example 32 to prepare a 20 wt % n-hexane solution thereof, and the solution was confirmed to be a homogeneous solution.

Example 33

Production of composition containing N,N-dihexadecyl-2,2,2-trifluoroethylammonium tetrakis(pentafluorophenyl)borate and ditetradecyl ether N,N-Dihexadecyl-2,2,2-trifluoroethylamine hydrochloride (8.10 g, 13.9 mmol) obtained in Production Example 40 was dissolved in dichloromethane (80 mL), ditetradecyl ether (8.10 g, 13.9 mmol) and lithium tetrakis(pentafluorophenyl)borate tri-diethyl ether complex (14.2 g, 13.7 mmol) was added, and the mixture was stirred at room temperature for 1 hr. Water was added to the reaction mixture, and the mixture was stirred at room temperature for 1 hr. The aqueous layer was separated, and the organic layer was washed with water. The organic layer was dried over anhydrous sodium sulfate, and then filtered, and the filtrate was concentrated under reduced pressure. The residue was dried under reduced pressure at 80° C. to give the title composition (22.5 g).

$^1$H NMR ($CDCl_3$) δ: 0.87-0.89 (12H, m), 1.20-1.80 (104H, m), 3.21-3.24 (4H, m), 3.38-3.41 (4H, m), 3.69 (2H, q);

$^{19}$F NMR ($CDCl_3$) δ: −66.7 (3F, br s), −134.0 (8F, m), −163.4 (4F, t), −167.5 (8F, t).

n-Hexane was added to the composition obtained in Example 33 to prepare a 20 wt % n-hexane solution thereof, and the solution was confirmed to be a homogeneous solution.

Example 34

Production of composition containing N,N-dihexadecyl-2,2,2-trifluoroethylammonium tetrakis(pentafluorophenyl)borate and didodecyl ether N,N-Dihexadecyl-2,2,2-trifluoroethylammonium tetrakis (pentafluorophenyl)borate (439.2 mg, 0.36 mmol) obtained in Example 25 was mixed with didodecyl ether (254 mg, 0.72 mmol), and n-hexane (1.756 g) was added to prepare a homogeneous hexane solution of the title composition. The solution was confirmed to be a homogeneous solution. This solution was concentrated under reduced pressure and analyzed by NMR.

$^1$H NMR ($CDCl_3$) δ: 0.87-0.91 (12H, m), 1.20-1.42 (100H, m), 1.53-1.69 (12H, m), 3.20-3.24 (4H, m), 3.40 (8H, t), 3.67 (2H, q);

$^{19}$F NMR ($CDCl_3$) δ: −66.9 (3F, t), −134.0 (8F, m), −163.8 (4F, t), −167.4 (8F, t).

Comparative Example 1

Attempts were made to prepare a 10 wt % methylcyclohexane solution or 10 wt % n-hexane solution of N,N-dimethylanilinium tetrakis(pentafluorophenyl)borate, but a homogeneous solution was not obtained. In the below-mentioned Experimental Example, N,N-dimethylanilinium tetrakis(pentafluorophenyl)borate was used as a co-catalyst in Comparative Example 1.

Comparative Example 2

Attempts were made to prepare a 10 wt % n-hexane solution of N,N-dioctadecylmethylammonium tetrakis(pentafluorophenyl)borate, but a homogeneous solution was not obtained. In the below-mentioned Experimental Example, N,N-dioctadecylmethylammonium tetrakis(pentafluorophenyl)borate was used as a co-catalyst in Comparative Example 2.

Experimental Example

Evaluation of Polymerization Performance

A general polymerization method using the compound or composition of the present invention as a co-catalyst is shown below.

Into 100 mL autoclave in a glove box were added 1-octene, triisobutylaluminum (TIBA, 0.55 M hexane solution), and a solvent (methylcyclohexane (MCH) or toluene) to give a comonomer solution. Dimethylsilylene(tert-butylamide)-(tetramethylcyclopentadienyl)-titanium (IV)-dichloride (CGC, polymerization catalyst), triisobutylaluminum (0.55 M hexane solution), and a solvent were added to prepare a catalyst solution at a predetermined concentration, and the solution was transferred to a Schlenk flask. The co-catalyst was dissolved in a solvent, and a co-catalyst solution at a predetermined concentration was prepared and transferred to the Schlenk flask. The comonomer solution, the catalyst solution, and the co-catalyst solution were mixed, and adjusted such that the total amount of the solvent and the total amount of triisobutylaluminum would be constant during the reaction. The inside of the autoclave was purged with ethylene, the catalyst solution and the co-catalyst solution were successively added to the autoclave, and the ethylene pressure was immediately adjusted to a predetermined pressure, and the mixture was stirred at a predetermined temperature (25° C. or 100° C.) for a predetermined time. The reaction mixture was ice-cooled, the ethylene gas was removed, the mixture was poured into methanol (100 mL) containing hydrochloric acid (3 mL), and the mixture was stirred at room temperature for 30 min. The precipitate was collected by filtration and dried under reduced pressure at 60° C. to give an ethylene-octene copolymer.

[Measurement of Melting Point]

Measurement by the differential scanning calorimetry method (DSC) was performed using DSC6220 instrument (Seiko Instruments Inc.). A sample (polymer) was heated at a rate of 10° C./min from 40° C. to 150° C., and the melting point was measured.

The results of the polymerization reaction at 25° C. and 100° C. are shown in Table 1 and Table 2, respectively.

TABLE 1

| co-catalyst | catalytic amount (μmol) | solvent | time (min) | yield (g) | activity (kg/mol of Ti · h) | melting point (° C.) |
|---|---|---|---|---|---|---|
| Comparative Example 2 | 0.1 | MCH | 6 | 0.033 | 3300 | 77.6 |
| Example 1 | 0.05 | MCH | 1.5 | 0.102 | 81600 | 70.5 |
| Example 2 | 0.05 | MCH | 1.5 | 0.134 | 107200 | 63.3, 68.0 |
| Example 4 | 0.05 | MCH | 1.5 | 0.253 | 202400 | 75.2 |
| Example 7 | 0.5 | MCH | 1.5 | 1.12 | 89960 | 80.3 |
| Example 11 | 0.1 | MCH | 1.5 | 0.465 | 185840 | 89.1 |
| Example 22 | 0.1 | MCH | 1.5 | 0.378 | 151200 | 71.5 |
| Comparative Example 1 | 0.1 | toluene | 1.5 | 0.85 | 340000 | 79.3 |
| Example 1 | 0.05 | toluene | 1.5 | 1.15 | 920000 | 84.0 |
| Example 4 | 0.05 | toluene | 1.5 | 1.23 | 984000 | 70.8 |

reaction conditions; catalyst: CGC, catalyst:co-catalyst = 1:1, TIBA (total amount 3000 μmol), total amount of solvent (40 mL), 1-octene (1 mL), ethylene pressure (8 atm), 25° C.

TABLE 2

| co-catalyst | catalytic amount (μmol) | solvent | time (min) | yield (g) | activity (kg/mol of Ti · h) | melting point (° C.) |
|---|---|---|---|---|---|---|
| Comparative Example 2 | 0.02 | MCH | 3 | 0.026 | 26000 | 90.0 |
| Example 1 | 0.02 | MCH | 3 | 0.460 | 460000 | 92.3 |
| Example 2 | 0.02 | MCH | 3 | 0.150 | 145300 | 93.2 |
| Example 22 | 0.02 | MCH | 3 | 0.330 | 333300 | 91.3 |

reaction conditions; catalyst: CGC, catalyst:co-catalyst = 1:1, TIBA (total amount 100 μmol), total amount of solvent (40 mL), 1-octene (1 mL), ethylene pressure (8 atm), 100° C.

According to Table 1 and Table 2, it was confirmed that the fluorine-containing ammonium borate compounds of Examples 1, 2, 4, 7, 11, and 22 showed higher polymerization activity than the compounds of Comparative Example 1 and Comparative Example 2 not containing a fluorine atom, regardless of the polymerization temperature and the kind of the solvent used. Furthermore, as shown in Table 1, the compositions (or complexes) of the present invention (Examples 1, 2, 4, and 22) afforded polymers having a lower melting point than Comparative Example depending on the polymerization conditions, and the uptake amount of comonomer is considered to have increased.

INDUSTRIAL APPLICABILITY

The compound or composition of the present invention shows high metal complex catalyst activation ability in the polymerization reactions of olefin, diene, and acetylene, and is useful as a co-catalyst. Also, according to the present invention, an industrial production method of the compound or composition of the present invention can also be provided.

This application is based on a patent application No. 2020-144177 filed in Japan (filing date: Aug. 28, 2020), a patent application No. 2020-196704 filed in Japan (filing date: Nov. 27, 2020), and a patent application No. 2021-037078 filed in Japan (filing date: Mar. 9, 2021), the contents of which are incorporated in full herein.

The invention claimed is:

1. A compound of formula (1):

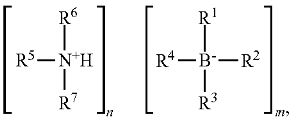

(1)

wherein $R^1$, $R^2$, $R^3$, and $R^4$ are each independently a $C_{6-14}$ aryl group substituted by one or more fluorine atoms or one or more fluoro $C_{1-4}$ alkyl groups, $R^5$ is a fluoro $C_{1-6}$ alkyl group $R^6$ and $R^7$ are each independently (a) a $C_{1-30}$ alkyl group optionally substituted by one or more substituents selected from the group consisting of (a1) a halogen atom, and (a2) a $C_{1-30}$ alkoxy group, or (b) a $C_{3-8}$ cycloalkyl group optionally substituted by one or more substituents selected from the group consisting of (b1) a halogen atom, (b2) a $C_{1-30}$ alkyl group, (b3) a $C_{1-30}$ alkoxy group, (b4) a halo $C_{1-30}$ alkyl group, and (b5) a halo $C_{1-30}$ alkoxy group, n is 1, m is 1, and a total carbon number of $R^5$, $R^6$, and $R^7$ is not less than 25.

2. The compound of claim 1, wherein $R^1$, $R^2$, $R^3$, and $R^4$ are each independently a phenyl group, a 1-naphthyl group, a 2-naphthyl group, a 2-biphenylyl group, a 3-biphenylyl group, a 4-biphenylyl group, a 1-anthryl group, a 2-anthryl group, a 9-anthryl group, a 9-phenanthryl group, or a 3-phenanthryl group, each of which is substituted by one or more fluorine atoms or one or more fluoro $C_{1-4}$ alkyl groups.

3. The compound of claim 1, wherein all of $R^1$, $R^2$, $R^3$ and $R^4$ are pentafluorophenyl groups, 2,2',3,3',4',5,5',6,6'-nonafluoro-4-(1,1'-biphenylyl) groups, 2,3,4,5,6,7,8-heptafluoro-1-naphthyl groups, or 1,3,4,5,6,7,8-heptafluoro-2-naphthyl groups.

4. A composition, comprising:

the compound of claim 1; and a compound of formula (2):

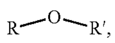

(2)

wherein

R and R' are each independently an optionally substituted $C_{1-30}$ alkyl group, an optionally substituted $C_{3-15}$ cycloalkyl group, or an optionally substituted $C_{6-14}$ aryl group.

5. The composition of claim 4, wherein R and R' are each independently an optionally substituted $C_{1-30}$ alkyl group.

6. The composition of claim 4, wherein a content of the compound of formula (2) with respect to 1 mole of the compound of formula (1) is in a range of from 0.01 to 10 mole.

7. The composition of claim 4, wherein a content of the compound of formula (2) with respect to 1 mole of the compound of formula (1) is in a range of from 0.1 to 3 mole.

8. A composition, comprising:

the compound of claim 1; and a compound of formula (3):

(3)

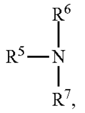

wherein $R^5$ is a fluoro $C_{1-6}$ alkyl group, $R^6$ and $R^7$ are each independently (a) a $C_{1-30}$ alkyl group optionally substituted by one or more substituents selected from the group consisting of (a1) a halogen atom, and (a2) a $C_{1-30}$ alkoxy group, or (b) a $C_{3-8}$ cycloalkyl group optionally substituted by one or more substituents selected from the group consisting of (b1) a halogen atom, (b2) a $C_{1-30}$ alkyl group, (b3) a $C_{1-30}$ alkoxy group (b4) a halo $C_{1-30}$ alkyl group, and (b5) a halo $C_{1-30}$ alkoxy group a total carbon number of $R^5$, $R^6$, and $R^7$ is not less than 25, and wherein the compound of formula (3) is an amine compound deprotonated from the cation constituting the formula (1).

9. The composition of claim 8, wherein a content of the compound of formula (3) with respect to 1 mole of the compound of formula (1) is in a range of from 0.01 to 10 mole.

10. The composition of claim 8, wherein a content of the compound of formula (3) with respect to 1 mole of the compound of formula (1) is in a range of from 0.5 to 3 mole.

11. The composition of claim 8, further comprising:

a compound of formula (2):

(2)

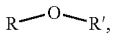

wherein

R and R' are each independently an optionally substituted $C_{1-30}$ alkyl group, an optionally substituted $C_{3-15}$ cycloalkyl group, or an optionally substituted $C_{6-14}$ aryl group.

12. A co-catalyst, comprising:

the compound of claim 1, wherein the co-catalyst is suitable for polymerizing an olefin, diene, acetylene, or a mixture of two or more of any of these.

13. A method for producing a polymer, the method comprising:

polymerizing at least one monomer selected from the group consisting of an olefin, diene, and acetylene, in the presence of the compound of claim 1 as a co-catalyst.

14. A co-catalyst, comprising:

the composition of claim 4, wherein the co-catalyst is suitable for polymerizing olefin, diene, acetylene, or a mixture of two or more of any of these.

15. A method for producing a polymer, the method comprising:

polymerizing at least one monomer selected from the group consisting of an olefin, diene, and acetylene, in the presence of the composition of claim 4 as a co-catalyst.

16. A method for producing a compound of formula (1):

(1)

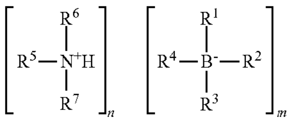

wherein $R^1$, $R^2$, $R^3$, and $R^4$ are each independently a $C_{6-14}$ aryl group substituted by one or more fluorine atoms or one or more fluoro $C_{1-4}$ alkyl groups, $R^3$ is a fluoro $C_{1-6}$ alkyl group, $R^6$ and $R^7$ are each independently (a) a $C_{1-30}$ alkyl group optionally substituted by one or more substituents selected from the group consisting of (a1) a halogen atom, and (a2) a $C_{1-30}$ alkoxy group, or (b) a $C_{3-3}$ cycloalkyl group optionally substituted by one or more substituents selected from the group consisting of (b1) a halogen atom, (b2) a $C_{1-30}$ alkyl group, (b3) a $C_{1-30}$ alkoxy group (b4) a halo $C_{1-30}$ alkyl group, and (b5) a halo $C_{1-30}$ alkoxy group n is 1, m is 1, and a total carbon number of $R^5$, Re, and $R^7$ is not less than 25, the method comprising:

reacting, in the presence of a protic acid, a compound of formula (4):

(4)

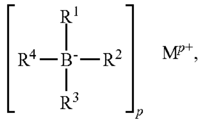

wherein $R^1$, $R^2$, $R^3$, and $R^4$ are as defined above, $M^{p+}$ is an alkali metal ion or an alkaline earth metal ion, and p is 1 or 2, with a compound of formula (3):

(3)

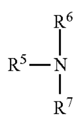

wherein $R^5$, Re and $R^7$ are as defined above.

* * * * *